(12) United States Patent
Sullivan

(10) Patent No.: US 8,450,473 B2
(45) Date of Patent: May 28, 2013

(54) COMPOSITIONS AND METHODS FOR THERAPY OF MACULAR DEGENERATION

(75) Inventor: Jack M. Sullivan, Hamburg, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 13/266,219

(22) PCT Filed: Apr. 30, 2010

(86) PCT No.: PCT/US2010/033107
§ 371 (c)(1),
(2), (4) Date: Mar. 9, 2012

(65) Prior Publication Data
US 2012/0202982 A1    Aug. 9, 2012

Related U.S. Application Data

(60) Provisional application No. 61/174,435, filed on Apr. 30, 2009.

(51) Int. Cl.
*C07H 21/04*    (2006.01)
(52) U.S. Cl.
USPC ........................................................ 536/24.5
(58) Field of Classification Search
USPC ........................................................ 536/24.5
See application file for complete search history.

(56) References Cited

U.S. PATENT DOCUMENTS

| | | |
|---|---|---|
| 6,225,291 B1 | 5/2001 | Lewin et al. |
| 6,255,071 B1 | 7/2001 | Beach et al. |
| 2002/0082225 A1 | 6/2002 | Blatt et al. |
| 2005/0096282 A1 | 5/2005 | Lewin et al. |
| 2005/0112095 A1 | 5/2005 | Hsu et al. |
| 2006/0121466 A1 | 6/2006 | Khvorova et al. |

OTHER PUBLICATIONS

Cullen, Bryan, Utility of the Secreted Placental Alkaline Phosphatase Reporter Enzyme, Methods in Enzymology, vol. 326, 2000: 159-160.
Citti, et al., Synthetic hammerhead ribozymes as therapeutic tools to control disease genes, Current Gene Therapy 2005, vol. 5: 11-24.
Khvorova, et al.; Sequence elements outside the hammerhead ribozyme catalytic core enable intracellular activity; Nature Structural Biology, vol. 10, No. 9, Sep. 2003; pp. 708-712.
Sullivan, et al.; Hammerhead ribozymes designed to cleave all human rod opsin mRNAs which cause autosomal dominant retinitis pigmentosa; Molecular Vision 2002, vol. 8; pp. 102-113.
Lieber, Andre, et al., Selection of Efficient Cleavage Sites in Target RNAs by Using a Ribozyme Expression Library, Molecular and Cellular Biology, Jan. 1995, vol. 15, No. 1, pp. 540-551.
Zakharchuk, et al.; The fowl adenovirus type 1 (CELO) virus-associated RNA-encoding gene: a new ribozyme-expression vector; Elsevier Science, 1995; pp. 189-193.
Sullivan, Jack M., et al., Bottlenecks in development of retinal therapeutic post-transcriptional gene silencing agents, Vision Research 48, Feb. 2008, vol. 48(3), pp. 453-469.
Abdelmaksoud, Heba E., et al., Development of lead hammerhead ribozyme candidates against human rod opsin mRNA for retinal degeneration therapy, Experimental Eye Research, May 2009, vol. 88(5), pp. 859-879.

*Primary Examiner* — Jon E Angell
(74) *Attorney, Agent, or Firm* — Hodgson Russ LLP

(57) ABSTRACT

Provided are compositions and methods for therapy of macular degeneration including dry age-related macular degeneration (dAMD), juvenile macular degenerations (JMDs) where toxic retinoids are known to accumulate as part of the pathogenesis, such as Stargardt disease, and Best disease, and neovascular wet age-related macular degeneration. The method entails administering to an individual in need of therapy for macular degeneration a first polynucleotide that can facilitate a reduction in the amount of rod opsin (RHO) mRNA in the individual; or a second polynucleotide that can facilitate a reduction in the amount of RPE65 mRNA in the individual; or a combination thereof. The polynucleotides of the invention are hammerhead ribozymes or shRNAs. The polynucleotides target a sequence in RHO mRNA or RPE65 mRNA and facilitate reduction in the target mRNA via ribozymatic cleavage of the target, or by hybridization to the target, which leads to RNAi mediated degradation of the target mRNA.

4 Claims, 10 Drawing Sheets

Figure 4.

Mouse *RPE65* Hammerhead Ribozyme Sequences

1. Mouse RPE65 UUC↓ 376 Hammerhead Ribozyme
5' TCGACGGTCTGG<u>CTGATGAGGCCGAAAGGCCGAAA</u>AAGCACCTGCA 3' (SEQ ID NO:24)
Targeted sequence (in bold below):
5' GUGCUUUC↓CCAGACC 3' (SEQ ID NO:25)

2. Mouse *RPE65* UUA↓ 480 Hammerhead Ribozyme
5' TCGACTGCATAG<u>CTGATGAGGCCGAAAGGCCGAAA</u>ATCTTCCTGCA 3' (SEQ ID NO:26)

Targeted sequence (in bold below):
5' GAAGAUUA↓CUAUGCA 3' (SEQ ID NO:27)

3. Mouse RPE65 GUC↓ 1183 Hammerhead Ribozyme
5' TCGACCTGTGTC<u>CTGATGAGGCCGAAAGGCCGAAA</u>CCTTGTCTGCA 3' (SEQ ID NO:28)

Targeted sequence (in bold below):
5' ACAAGGUC↓GACACAG 3' (SEQ ID NO:29)

The first four nucleotides are designed to ligate into a XhoI site and the last four nucleotides are designed to ligate into a Pst I site in the vector. The underlined sequences are the core of the hammerhead ribozyme. The core sequences of the hammerhead ribozyme are flanked by antisense sequences (not underlined) that anneal to the targeting sequence in the *RPE65* mRNA.

Human *RPE65* 221 shRNA:

Figure 6

Human *RPE65* 520 shRNA:

5'- AAUCCAGAGACCUUGGAGAUUCAAGAGAUCUCCAAGGUCUCUGGAUUUU-3'

(SEQ ID NO:31)

```
                          U   C
                       U       A
5'- AAUCCAGAGACCUUGGAGA         A    shRNA 520
3'- UUUUAGGUCUCUGGAACCUCU       A
                        A     G
                         G   A
                          A
```

Figure 7

Human *RPE65* 933 shRNA:

5'-CAAAAAAGGAAAAAGUACUUCAAGAGAGUACUUUUUCCUUUUUUUGUU-3'

(SEQ ID NO:32)

```
                                        U  U  C
                                                  A
5'- CAAAAAAGGAAAAAGUAC                            A    shRNA 933
3'- UUGUUUUUUUCCUUUUUCAUG                         A
                                         A       G
                                           G   A
                                             A
```

Figure 8

Human *RPE65* 2108 shRNA:

5'-CCAAACUUUUUCUCAAACCUUCAAGAGAGGUUUGAGAAAAGUUUGGUU-3'

(SEQ ID NO:33)

```
                              U U C
5'- CC AAACUUUUUCUCAAACC  U       A
3'- UUGGUUUGAAAAAGAGUUUGG          A     shRNA 2108
                          A     G
                           G A A
```

Human *RHO* 725 shRNA (SEQ ID NO:21)

ved a 28.97% knockdown of SEAP reporter protein activity in the stable Rho-IRES-SEAP cell line, and resides in a region we found to be highly accessible by in silico and experimental assays of accessibility.

COMPOSITIONS AND METHODS FOR THERAPY OF MACULAR DEGENERATION

This application claims priority to U.S. application Ser. No. 61/174,435, filed on Apr. 30, 2009, the entire disclosure of which is incorporated herein by reference.

This invention was made with government support under R01 EY13433 awarded by the National Eye Institute. The government has certain rights in the invention.

BACKGROUND OF THE INVENTION

Macular degeneration is a clinical term that is used to describe a family of diseases that are all characterized by a progressive loss of central vision associated with abnormalities of Bruch's membrane, the choroid, the neural retina and/or the retinal pigment epithelium. These disorders include very common conditions that affect older subjects (age-related macular degeneration or AMD) as well as rarer, earlier-onset dystrophies that in some cases can be detected in the first decade of life. Other maculopathies include and dry age-related macular degeneration (dAMD), juvenile macular degenerations (JMDs) where toxic retinoids are known to accumulate as part of the pathogenesis (e.g., Stargardt disease, and Best disease), neovascular and wet age-related macular degeneration.

Age-related macular degeneration (AMD), the most prevalent macular degeneration, is associated with progressive diminution of visual acuity in the central portion of the visual field, changes in color vision, and abnormal dark adaptation and sensitivity. Two principal clinical manifestations of AMD have been described as the dry, or atrophic, form, and the wet, or exudative, form. Dry AMD is the most common form of macular degeneration and affects millions of people in the US alone. There is an ongoing and unmet need for therapies of macular degeneration.

SUMMARY OF THE INVENTION

The present invention provides compositions and methods for therapy of macular degeneration. The method comprises administering to an individual in need of therapy for macular degeneration a composition comprising i) a first polynucleotide that can facilitate a reduction in the amount of rod opsin (RHO) mRNA in the individual; or ii) a second polynucleotide that can facilitate a reduction in the amount of RPE65 mRNA in the individual; or iii) a combination of i) and ii). Performance of the method of the invention results in macular degeneration in the individual being inhibited.

The polynucleotides of the invention are hammerhead ribozymes or shRNAs. The polynucleotides target a sequence in RHO mRNA or RPE65 mRNA and facilitate reduction in the target mRNA via ribozymatic cleavage of the target, or by hybridization to the target, which leads to RNAi mediated degradation of the target mRNA.

The forms of macular degeneration that the individual who is treated using the method of the invention include but are not necessarily limited to dry age-related macular degeneration (dAMD), juvenile macular degenerations (JMDs) where toxic retinoids are known to accumulate as part of the pathogenesis (e.g., Stargardt disease, and Best disease), and neovascular wet age-related macular degeneration.

DESCRIPTION OF THE FIGURES

FIG. 4 provides a description of mouse RPE65 Hammerhead Ribozyme Sequences and the sequences they target.

FIG. 6 provides a description of an shRNA that targets human RPE65 at site 520 (Human RPE65 520 shRNA).

FIG. 7 provides a description of an shRNA that targets human RPE65 at site 933 (Human RPE65 933 shRNA).

FIG. 8 provides a description of an shRNA that targets human RPE65 at site 2108 (RPE65 2108 shRNA).

DETAILED DESCRIPTION OF THE INVENTION

Figure 1:
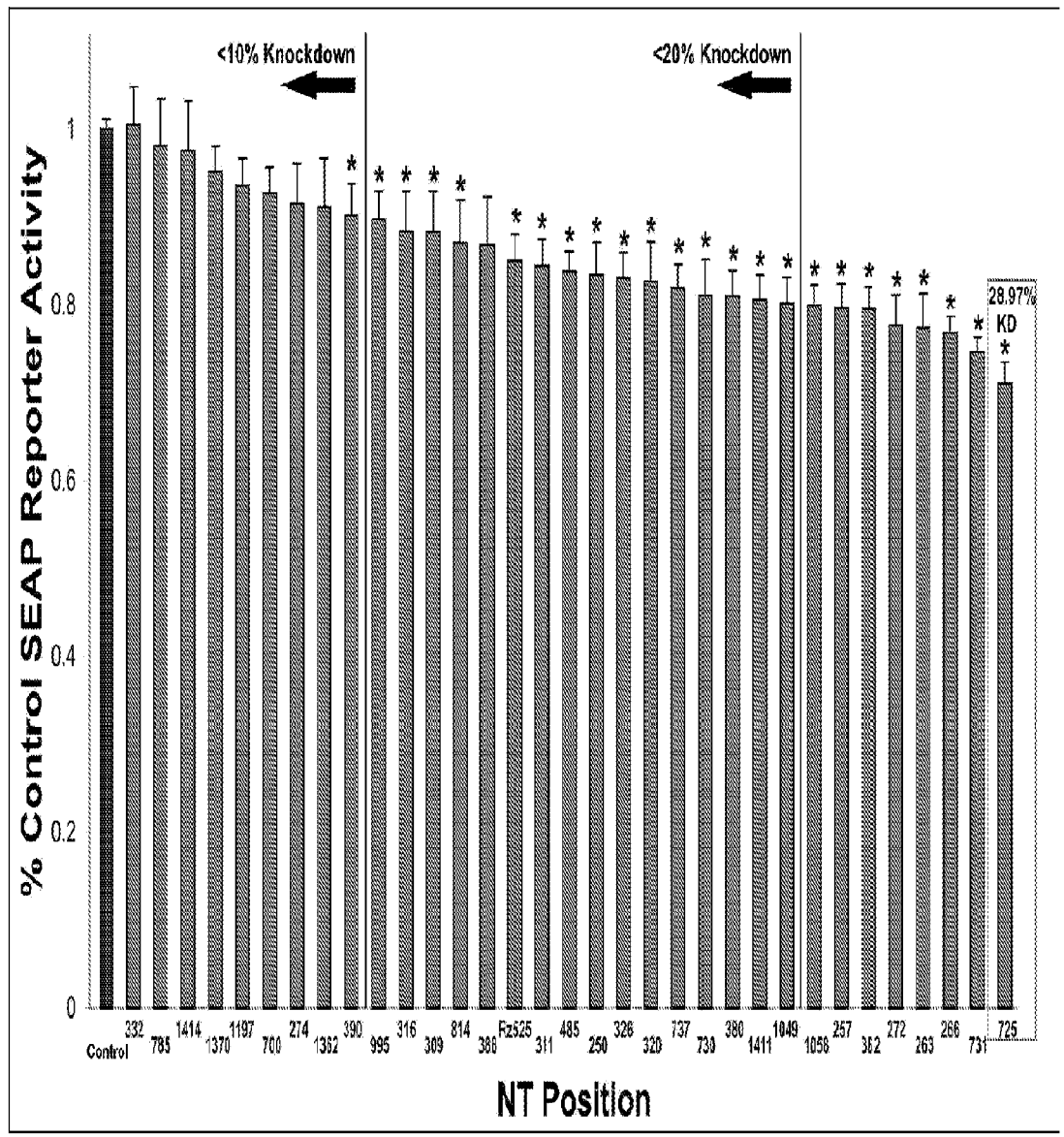
FIG. 1 provides a graphical representation of rank order of candidate opsin ribozyme NUH sites by SEAP assay. Of 34 hhRzs tested, 25 significantly reduced SEAP protein expression ($p<0.01$, $n=8$). These sites were rank ordered based on amount of SEAP activity knockdown. The target site at 725 showed a 28.97% knockdown of SEAP reporter protein activity in the stable Rho-IRES-SEAP cell line, and resides in a region we found to be highly accessible by in silico and experimental assays of accessibility.

The present invention provides compositions and methods for therapy of macular degeneration. The method comprises administering to an individual in need of therapy for macular degeneration a composition comprising:

i) a first polynucleotide that can facilitate a reduction in the amount of rod rhodopsin (RHO) mRNA in the individual; or ii) a second polynucleotide that can facilitate a reduction in the amount of RPE65 mRNA in the individual; or iii) a combination of i) and ii);

wherein macular degeneration in the individual is inhibited subsequent to the administration. Those skilled in the art can readily determine whether macular degeneration has been inhibited using any of a variety of well known clinical and/or molecular biological techniques.

The invention is based in part on the disease etiology of several forms of macular degeneration that are caused by and/or positively correlated with accumulation of toxic retinoids. The forms of macular degeneration for which the present invention is expected to provide a therapeutic benefit include but are not necessarily limited to dry age-related macular degeneration (dAMD), juvenile macular degenerations (JMDs) where toxic retinoids are known to accumulate as part of the pathogenesis (e.g., Stargardt disease, and Best disease), and neovascular wet age-related macular degeneration. Thus, in various embodiments, the method comprises administering a composition comprising a first polynucleotide that can facilitate a reduction in the amount RHO mRNA in the individual, or a second polynucleotide that can facilitate a reduction in the amount of RPE65 mRNA in the individual, or a combination of such polynucleotides, to an individual in need of therapy for a macular degeneration, wherein the macular degeneration is selected from dAMD, JMDs where toxic retinoids are known to accumulate as part of the pathogenesis, and wet neovascular age-related macular degeneration. In one embodiment, the individual does not have and/or has not previously been treated for an eye disorder that is not a macular degenerative disorder, such as retinitis pigmentosa.

Polynucleotides that can "facilitate a reduction in mRNA" encompass RNA polynucleotides or and/or modified RNA polynucleotides that can participate in a biological process that results in degradation of RHO mRNA and/or RPE65 mRNA. It will be recognized that the net result of mRNA degradation is a reduction in the intracellular amount of protein encoded by the mRNAs. Thus. the invention provides a method for post-transcription gene silencing (PTGS) of the RHO and RPE65 genes.

In various embodiments, the polynucleotide that can facilitate a reduction in the amount of mRNA is a ribozyme, such as a hammerhead ribozyme ("hhRz") or a hairpin ribozyme, or an shRNA. It will thus be apparent that the polynucleotide that can facilitate a reduction in the amount of mRNA may act directly on the mRNA to catalyze its degradation (e.g., a ribozyme), or it may facilitate reduction in the amount of mRNA by hybridization to the mRNA to direct the mRNA to an RNAi-mediated degradation pathway. For instance, in one embodiment, the method comprises administering to an individual a first shRNA polynucleotide targeted to RHO mRNA, and/or a second shRNA polynucleotide targeted to RPE65 mRNA. As is known in the art, shRNAs adopt a typical secondary structure that contains a paired sense and antisense portion, and a short loop sequence between the paired sense and antisense portions. shRNA is delivered to the cytoplasm where it is processed by dicer into siRNAs. The siRNAs are recognized by RNA-induced silencing complex (RISC), and once incorporated into RISC, siRNAs facilitate cleavage and degradation of targeted mRNA. Each of the shRNAs used in the present invention can consist of between 45-100 nucleotides, inclusive, and including all integers between 45 and 100.

In the case of a ribozyme that can cleave a target mRNA, the ribozyme binds to an accessible region of the target mRNA, cleaves it, and then dissociates from the target and performs the same series of reactions (enzymatic turnover) with other substrate mRNA molecules. Ribozymes generally bind to target RNA with sufficient strength to insure a hybrid lifetime that allows chemical cleavage of target RNA, but not so strongly that the product dissociation is slow and inhibits turnover (product inhibition). Hammerhead ribozymes are known to cleave at a consensus sequence triplet with a central U which can be described as NUI↓, where N can be any nucleotide and H any nucleotide but G, and where the arrow identifies the cleavage site.

The invention provides multiple novel shRNAs and ribozymes that target RHO mRNA or RPE65 mRNA. Further, shRNAs that are directed to each of these mRNAs are commercially available. For example, THERMO SCIENTIFIC Open Biosystems offers a variety of shRNs against human and mouse RPE65 mRNA (i.e., GenBank entries NM_000329 and NM_029987, respectively). The same entity offers a variety of shRNAs against human and mouse RHO mRNA (i.e., GenBank entries NM_000539 and NM_145383, respectively).

Additionally, the method comprises ribozymes and shRNAs that can cleave target mRNA at a specific site, or cause a target mRNA to be degraded via RNAi-medicated RNA degradation. For instance, in one embodiment, the method employs a ribozyme that cleaves an mRNA comprising the sequence of SEQ ID NO:1, wherein the cleavage occurs between nucleotides 725 and 726 of SEQ ID NO:1.

The method also comprises administering one or more viral vectors encoding a polynucleotide that can facilitate a reduction in the amount of RHO mRNA in the individual and/or encoding a polynucleotide that can facilitate a reduction in the amount of RPE65 mRNA in the individual. In this regard, any viral vector or nanoparticle vector capable of expressing the coding sequences for the polynucleotides can be used. Examples of suitable vectors include but are not limited to viral based vectors, such as adenovirus (AV) vectors, adeno-associated virus (AAV) vectors, retroviral vectors [e.g, lentiviruses (LV) or murine leukemia virus], rhabdoviruses [rabies virus or vesicular stomatitis virus (VSV)]. In one embodiment, a chicken adenovirus (CELO virus) may be used. In another embodiment, recombinant adeno-associated virus (rAAV) type with high specificity for photoreceptor transduction (rAAV2-7 or rAAV2-8) is used. As used herein, "administering" an shRNA or a ribozyme is intended to encompass administering a vector encoding the shRNA or the ribozyme that is transcribed from the vector. The first and second polynucleotides can be encoded by the same or distinct vectors.

The method of the invention can be performed by administering the polynucleotides as naked polynucleotides, or in combination with any suitable pharmaceutically acceptable carriers, excipients and/or stabilizers. Some suitable examples of pharmaceutically acceptable carriers, excipients and stabilizer can be found in *Remington: The Science and Practice of Pharmacy* (2005) 21st Edition, Philadelphia, Pa. Lippincott Williams & Wilkins.

The method can also be performed by administering the polynucleotides with a delivery agent. Suitable delivery agents include but are not limited to the Mirus Transit TKO lipophilic reagent; lipofectin; lipofectamine; cellfectin; or polycations (e.g., polylysine), or liposomes.

In one embodiment, the polynucleotides are administered via intraocular injection (e.g., sub-retinal injection), but the administration may be performed by any other suitable route, including but not limited to an eye-drop solution, an implantable composition, a time-release composition, or any other suitable method and/or composition. The polynucleotides can be delivered as a single dose or as multiple doses over days, weeks, months, or longer. The administrations can occur simultaneously or sequentially in any order. In one embodiment, there is an opportunity for multiple PTGS agents that target independent accessible regions of a single target to enhance the a reduction in target mRNA, and such enhancement may be greater than additive (i.e., it may result in a synergistic effect).

Polynucleotides for the compositions and methods of the invention can be made using any acceptable technique, including conventional and commercially available chemical synthesis techniques, in vitro transcription, etc., such as by expression from expression vectors, and isolated and purified as necessary or desired. Further, various types of polynucleotide modifications are contemplated so as to improve the capability of the polynucleotides to resist endonuclease degradation and/or improve facilitation of reduction of their mRNA targets. For example, in addition to RNA, the polynucleotides can comprise RNA:DNA hybrids. Other modifications that can be comprised by the polynucleotides include but are not limited to modified ribonucleotides or modified deoxyribonucleotides. Such modifications can include without limitation substitutions of the 2' position of the ribose moiety with an —O— lower alkyl group containing 1-6 saturated or unsaturated carbon atoms, or with an —O-aryl group having 2-6 carbon atoms, wherein such alkyl or aryl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group. In addition to phosphodiester linkages, the nucleotides can be connected by a synthetic linkage, i.e., inter-nucleoside linkages other than phosphodiester linkages. Examples of inter-nucleoside linkages that can be used in the invention include but are not limited to phosphodiester, alkylphosphonate, phosphorothioate, phosphorodithioate, phosphate ester, alkylphosphonothioate, phosphoramidate, carbamate, carbonate, morpholino, phosphate trister, acetamidate, carboxymethyl ester, or combinations thereof.

The invention also provides compositions comprising polynucleotides that can facilitate a reduction in the amount of RHO mRNA in the individual and/or that can facilitate a reduction in the amount of RPE65 mRNA via ribozymatic activity or via RNAi mediated mRNA degradation. The polynucleotides can be any of those discussed supra as suitable for being used in the method of the invention, and accordingly include shRNAs, ribozymes, and vectors that encode such polynucleotides. Representative polynucleotide sequences that the compositions can comprises are described more fully below. The compositions can comprise, consist essentially of, or consist of shRNAs, ribozymes, or viral vectors encoding the same.

The pathogenesis and symptomology of the forms of macular degeneration for which the present invention provides therapeutic compositions and methods are well characterized. In general, in orphan JMDs (e.g. Stargardt, Best) and common dAMD there is accumulation of cellular and biochemical debris within and beneath the RPE. Each day the distal tips (10%) of rod and cone PR outer segment are shed according to a circadian cycle. Expression and trafficking of new phototransduction and cellular materials maintains the outer segment length and structure to support scotopic and photopic realms of human vision. In the rod rich parafoveal area of the human retina, where both dAMD and JMDs begin (1-3 mm from fovea, 3.5-10° eccentricity from fixation), there are approximately 30-40 PRs per single RPE cells and most of these are rods. The RPE cell phagocytizes the distal PR tips for lysosomal digestion. This intracellular digestion process is incomplete and results in accumulation of outer segment materials in RPE phagolysosomes including retinoids. This material is called lipofuscin (LF). LF is composed of numerous protein, lipid and carbohydrate components. LF accumulates in the RPE over time as the individual ages. Materials in LF contribute to sub-RPE deposits such as flecks and drusen in juvenile macular degenerations and dry AMD. LF has a brilliant autofluorescence under blue light excitation due to the presence of a bis-retinoid pyridinium salt, N-retinylidene-N'-retinyl-ethanolamine (A2E), and retinaldehyde dimers (RetDi). The process of A2E and RetDi formation occurs spontaneously in the PR outer segments, and is derived from the chemical covalent ligation of two molecules of all-trans-retinal (ATR) with a single molecule of the membrane aminolipid, PE.

ATR forms because light bleaches rod and cone visual pigments. Because of finite enzymatic limits within the retinoid visual cycle, some unknown fraction of the total ATR that forms has sufficient time to react with PE, and/or another ATR molecule, to form A2E and RetDi. Precursors to A2E/RetDi form in outer segments and are a component of shed rod and cone outer segment tips and the completion of formation of A2E/RetDi occur in the RPE phagolysosome. Due to their unique structures these chemicals cannot be metabolized and accumulate in RPE cells over time. Accumulation reflects the normal daily production of ATR from the visual cycle, which varies with light exposure, and normal RPE phagocytosis of PR outer segment tips, integrated over many years. In the case of juvenile MD or dAMD the rate of accumulation of A2E/RetDi is greatly accelerated, and thus can be used to define an individual in need of the presently provided compositions and methods. Additionally, RPE cells in these diseases become physically swollen with numerous engorged phagolysosomes such that their surface area expands. While RPE cells may secrete some of this material onto underlying Bruch's membrane and contribute to formation of the drusen of dAMD or the flecks or yolk-like accumulations in JMDs, the prevailing model is that death of focal RPE cells deposits undigested bulk material onto Bruch's membrane that forms clinically visible lesions of these syndromes. The accumulation of A2E, retinal dimer, and other toxic retinoids in the RPE cells also has a direct toxic influence on these cells and can directly promote cell death. As RPE cells are post-mitotic, surrounding cells do not divide after local neighbor loss, but rather expand and spread out to fill the void in the RPE matrix and reconstitute the outer blood-retinal barrier. In doing so, single RPE cells cover larger areas and more PRs, which compounds the cumulative daily stress to fewer cells that must provide for nutrient exchange from the choroid, phagocytosis of outer segment tips, and retinoid metabolism. With progressive local death in the RPE matrix, there are insufficient numbers to sustain PR coverage and a stable hole in the matrix is formed. Overlying PRs without the critical interaction with the underlying RPE cells die secondarily. This results in focal areas of visual sensitivity loss in the JMDs, or the emergence of geographic atrophy of end stage dAMD. These areas expand with disease progression and A2E accumulates in RPE cells at the edge of the wake of geographic atrophy prior to RPE and PR cell death. Thus, the present provides a therapy for forms of macular degeneration that are caused by, or are positively correlated with, the accumulation of toxic retinoids, and the invention embraces a metabolic engineering approach that can reduce the accumulation of the toxic retinoids.

It is notable that within the rod-rich human parafovea, where A2E/RetDi accumulates and JMDs and dAMD begin, a single human RPE cell overlies 30-40 rod PRs and only a few cone PRs. This reflects the absolute numbers of rods ($120 \times 10^6$) and cones ($6-7 \times 10^6$) in the human retina, and their nonuniform distribution. JMDs and dAMD originate in the parafoveal region of the retina where the rod density is high and the foveal cone density has already fallen strongly. With 10% of the volume of outer segments of rod or cone PRs being shed each day, a single RPE cell phagocytizes the equivalent of 2.5 full rod PR outer segments and 0.1 cone PR outer segments per day. The RPE is one of the most metabolically active cells in the human body. The parafoveal RPE is presented with 25-fold greater rod than cone mass material on a daily basis. Light bleached visual pigment is the source of essentially all ATR molecules that might form A2E/RetDi. Thus, the invention takes advantage of the novel discovery that decreased stress on the parafoveal RPE and RPE in general should result in decreases in the bulk mass of rod outer segment material that is presented to the RPE by its local associated population of rod PRs. Therefore, by reducing the overall metabolic load on the RPE, stress levels will be lower, and the probability of both RPE and PR cell death will decrease accordingly. The invention also takes advantage of the discovery that decreased amounts of A2E/RetDi should be formed if there were both decreased levels of visual pigment to form ATR during bleaching, and decreased turnover (bleaching followed by recovery) of the available levels of rod visual pigment integrated over many cycles into the life of the individual. Accordingly, and without intending to be bound by theory, it is expected that by decreasing the steady-state level of total retinoid molecules in the rod-RPE retinoid visual cycle that are available to form ATR, the level of A2E/RetDi that otherwise forms from two serial $2^{nd}$-order biochemical reactions should decrease significantly, and this would reduce the toxic impact on RPE structure and metabolism.

In view of the foregoing, it will be apparent to those skilled in the art that post-transcriptional gene silencing (or reducing the level of mRNA) for RHO and RPE65 should confer a therapeutic benefit for individuals who suffer the aforementioned biochemical/ocular irregularities that lead to macular degeneration associated therewith. In more detail, and again without intending to be bound by any particular theory, it is believed that A2E-mediated or toxic retinoid-mediated RPE toxicity in dAMD or JMDs can be slowed by programming kinetic bottlenecks in the generation and metabolic processing of ATR. In particular, suppressing a fraction of RHO expression specifically in rod photoreceptors would clamp a major source of ATR formation that leads to A2E and other toxic retinoids. Likewise, suppressing a fraction of RPE65 in RPE would clamp turnover of retinoid backbones in visual pigment regeneration.

PTGS in particular cell types is a highly specific means of reducing levels of target mRNAs and proteins to modulate distributed cellular system functionality, but RNA biocomplexity limits development of potent and safe PTGS agents as mRNA targets which are densely folded and large, stable, single-stranded PTGS annealing platforms are rare. We developed and utilize here a proven platform of high throughput screening technologies to: 1) identify rare strongly accessible regions in target mRNAs, 2) screen sets of PTGS agents in cultured cell expression systems to identify lead candidates, and 3) optimize polynucleotides that can facilitate a reduction in RHO and RPE65 mRNA. The screening procedure is described in US patent publication no. 20080227103, the entire disclosure of which is incorporated herein by reference.

In the present invention, we achieved highly potent ribozyme and shRNA PTGS agents against RHO mRNA (90% suppression). For RPE65, substantial and significant target suppression was achieved.

Human rod opsin mRNA (transcribed from the RHO gene) has the following sequence:

```
                                                         (SEQ ID NO: 1)
AGAGUCAUCCAGCUGGAGCCCUGAGUGGCUGAGCUCAGGCCUUCGCAGCAUUCUUGGGUG

GGAGCAGCCACGGGUCAGCCACAAGGGCCACAGCCAUGAAUGGCACAGAAGGCCCUAACU

UCUACGUGCCCUUCUCCAAUGCGACGGGUGUGGUACGCAGCCCCUUCGAGUACCCACAGU

ACUACCUGGCUGAGCCAUGGCAGUUCUCCAUGCUGGCCGCCUACAUGUUUCUGCUGAUCG

UGCUGGGCUUCCCCAUCAACUUCCUCACGCUCUACGUCACCGUCCAGCACAAGAAGCUGC

GCACGCCUCUCAACUACAUCCUGCUCAACCUAGCCGUGGCUGACCUCUUCAUGGUCCUAG

GUGGCUUCACCAGCACCCUCUACACCUCUCUGCAUGGAUACUUCGUCUUCGGGCCCACAG

GAUGCAAUUUGGAGGGCUUCUUUGCCACCCUGGGCGGUGAAAUUGCCCUGUGGUCCUUGG

UGGUCCUGGCCAUCGAGCGGUACGUGGUGGUGUGUAAGCCCAUGAGCAACUUCCGCUUCG

GGGAGAACCAUGCCAUCAUGGGCGUUGCCUUCACCUGGGUCAUGGCGCUGGCCUGCGCCG

CACCCCCACUCGCCGGCUGGUCCAGGUACAUCCCCGAGGGCCUGCAGUGCUCGUGUGGAA

UCGACUACUACACGCUCAAGCCGGAGGUCAACAACGAGUCUUUUGUCAUCUACAUGUUCG

UGGUCCACUUCACCAUCCCCAUGAUUAUCAUCUUUUUCUGCUAUGGGCAGCUCGUCUUCA

CCGUCAAGGAGGCCGCUGCCCAGCAGCAGGAGUCAGCCACCACACAGAAGGCAGAGAAGG

AGGUCACCCGCAUGGUCAUCAUCAUGGUCAUCGCUUUCCUGAUCUGCUGGGUGCCCUACG

CCAGCGUGGCAUUCUACAUCUUCACCCACCAGGGCUCCAACUUCGGUCCCAUCUUCAUGA

CCAUCCCAGCGUUCUUUGCCAAGAGCGCCGCCAUCUACAACCCUGUCAUCUAUAUCAUGA

UGAACAAGCAGUUCCGGAACUGCAUGCUCACCACCAUCUGCUGCGGCAAGAACCCACUGG

GUGACGAUGAGGCCUCUGCUACCGUGUCCAAGACGGAGACGAGCCAGGUGGCCCCGGCCU

AAGACCUGCCUAGGACUCUGUGGCCGACUAUAGGCGUCUCCCAUCCCCUACACCUUCCCC

CAGCCACAGCCAUCCCACCAGGAGCAGCGCCUGUGCAGAAUGAACGAAGUCACAUAGGCU

CCUUAAUUUUUUUUUUUUUUUAAGAAAUAAUUAAUGAGGCUCCUCACUCACCUGGGACA

GCCUGAGAAGGGACAUCCACCAAGACCUACUGAUCUGGAGUCCCACGUUCCCCAAGGCCA

GCGGGAUGUGUGCCCCUCCUCCUCCCAACUCAUCUUUCAGGAACACGAGGAUUCUUGCUU

UCUGGAAAAGUGUCCCAGCUUAGGGAUAAGUGUCUAGCACAGAAUGGGGCACACAGUAGG

UGCUUAAUAAAUGCUGGAUGGAUGCAGGAAGG.
```

The sequence of mouse rod opsin mRNA is as follows:

(SEQ ID NO: 2)

```
   1 CGUCAGUGGC UGAGCUCGCC AAGCAGCCUU GGUCUCUGUC UACGAAGAGC CCGUGGGGCA
  61 GCCUCGAGAG CCGCAGCCAU GAACGGCACA GAGGGCCCCA AUUUUUAUGU GCCCUUCUCC
 121 AACGUCACAG GCGUGGUGCG GAGCCCCUUC GAGCAGCCGC AGUACUACCU GGCGGAACCA
 181 UGGCAGUUCU CCAUGCUGGC AGCGUACAUG UUCCUGCUCA UCGUGCUGGG CUUCCCCAUC
 241 AACUUCCUCA CGCUCUACGU CACCGUACAG CACAAGAAGC UGCGCACACC CCUCAACUAC
 301 AUCCUGCUCA ACUUGGCCGU GGCUGACCUC UUCAUGGUCU UCGGAGGAUU CACCACCACC
 361 CUCUACACAU CACUCCAUGG CUACUUCGUC UUUGGGCCCA CAGGCUGUAA UCUCGAGGGC
 421 UUCUUUGCCA CACUUGGAGG UGAAAUCGCC CUGUGGUCCC UGGUGGUCCU GGCCAUUGAG
 481 CGCUACGUGG UGGUCUGCAA GCCGAUGAGC AACUUCCGCU UCGGGGAGAA UCACGCUAUC
 541 AUGGGUGUGG UCUUCACCUG GAUCAUGGCG UUGGCCUGUG CUGCUCCCCC ACUCGUUGGC
 601 UGGUCCAGGU ACAUCCCUGA GGGCAUGCAA UGUUCAUGCG GGAUUGACUA CUACACACUC
 661 AAGCCUGAGG UCAACAACGA AUCCUUUGUC AUCUACAUGU UCGUGGUCCA CUUCACCAUU
 721 CCUAUGAUCG UCAUCUUCUU CUGCUAUGGG CAGCUGGUCU UCACAGUCAA GGAGGCGGCU
 781 GCCCAGCAGC AGGAGUCAGC CACCACUCAG AAGGCAGAGA AGGAAGUCAC CCGCAUGGUU
 841 AUCAUCAUGG UCAUCUUCUU CCUGAUCUGC UGGCUUCCCU ACGCCAGUGU GGCCUUCUAC
 901 AUCUUCACCC ACCAGGGCUC CAACUUCGGC CCCAUCUUCA UGACUCUGCC AGCUUUCUUU
 961 GCUAAGAGCU CUUCCAUCUA UAACCCGGUC AUCUACAUCA UGUUGAACAA GCAGUUCCGG
1021 AACUGUAUGC UCACCACGCU GUGCUGCGGC AAGAAUCCAC UGGGAGAUGA CGACGCCUCU
1081 GCCACCGCUU CCAAGACGGA GACCAGCCAG GUGGCUCCAG CCUAAGCCUG GCCAGAGACU
1141 GUGGCUGAAA GUAGGAGUCU CCUGUCCCCA CACACCCCAG CCACAGCCCC CACCAGGAGC
1201 AGCACCCGUU GGGAUGAGGU CAUGCAGGCU CCCUCAGUGU CUUUUCUUU GUUUUUAAUG
1261 AAUUCAUGAA AGCAAAAUGA GGCUCCCCAC UCAAUGGGGA CAGCUUGACA AAGGGCAUCC
1321 AUCCACCAAG ACCAUCCUCA ACCUGGAGUC CCCAAUUCCC GGGGGGCCAG CGGGAUCUGU
1381 ACCCCUCCCU CAGCUUGUCU AUCAGGAACA UGACAAGUGU CCCGGCUUAG GGCUAAAUGU
1441 CUAGGACAGA AUGGAACACA UAGUAGCUGA UUAAUAAAUG CUAGCUGGAU GAAGGGAGGA
1501 AUGAGUGACU GACUGAGUGG AUAUAUGAGU GAAGGGAUUA AUGGAAGGGA ACAUGGAUGU
1561 CCUCAGGUGC CCAACCUGGC AGAUCCAGUC AUGUCUGGCU GGAAUCUAUA AGCAGUUUUA
1621 CAUACCUGCC CUGGUUUUCU CUGCCCCCAC CCCCACCCCA GUUGGAUCUC CCAAAUCCAG
1681 GGCCCUGAUA GAAUAUGGCU GCUUCAAAGA CAGAGAGAUG AGGGGAGGGA GGGGGGAGGG
1741 AGAGAGGGAG GGAGGGAGAC ACAGAGAGGG AAUAUGUGUG AUGCGUGUGU AUGUGUGUAU
1801 GUGUGUGUGU AAACACUUUG UAUAUAAAGA GUACAGCUGG UAGUUAUGUU ACAAGUAACA
1861 CCGACUAAUA UAAUUAAUUA ACCAUCCUAA UGGUCUCUGC UUGUUAGUGA CUGCUUGGGA
1921 AUUAGGCAGG GCCCAAGCAC UCAGAUAAGG UAUUUCCCUC AGCCUCAGUA GGCUUUUGCA
1981 AAUGACCCAG GCCUUCAGGC CUGUGCAGGG CUAGAGCUGG AUUACAGAGA UAAAUGACAG
2041 UGACAGCAAC GUGAGCUGCA GCCCUUAGGA CUGAGAAAGC AUCGAGACCA GGGGUCUCCG
2101 GCAAGGCCUA GGUCCUCCCU UCAGUAUGGA AACCUUGCCU CAUGUCUCUC AGCCUCCUUG
2161 GCCUGUGGAG AUCCAGCCCU UCCUCUUGGC UUCUGGAUAC AUUUGCUCUU CUACACCAGC
2221 AACCAAGUGU CAACAGUUCC AGGCCAGUAU GGAGUUUUAG AAGCCAUGCC AAUAUGCCCA
2281 CCUUCAGGGA GCAGCUGAGU CCUUGAUGCC ACCCUUGUUC UGAAGAGUUC AGAAACACAG
```

```
2341 UGCAAGACAU GACCAGGCCU CAUCCUUAGG AUGCUCAUGG AUCCAGUUCU UAGCUCCCUU

2401 GUUGGAUAUG CUGUUUUCCU UGGCCUUUGG UCUUUUCUUU AUCCCAGAGG GUUUUGGCUU

2461 UAAGGCCAAC AGGAACUAUG GGGUACCAGA AUUGAGCAGC CUCAGUCUGC AUCCCUCCUC

2521 UAUAGAACCA CAGCUGGGCC CUCAGCAGGG CCAACUCUGC AUGGGACAG AGGCAUUAAA

2581 AGCUCAGCUC CUACACUUGG UGGCAGUGGU GGUCUGUUGC UCUCAAGCUC UUUCAAAAUG

2641 GAUGGAAACU GGGACGCUUC CCUGACCCCU GGUUAUGAAA GACUAGACUG UGUGGGGACA

2701 AACAGUCCAG AGUCCCGGGG AAUGUGAUAG AGCAGCUCCA UCAUUUUUAG AAACCCAAUU

2761 UGAGGCAGUA UAGAGAGAUG GUGACCUCUA UAAGCCUCUG UAUCUGCAAA GAGGAGCUUA

2821 GACCUGCCCU UGAGGGGAUU AUAUGAGAUU UAAGGGACUU AUGUGGCCAG CCUACUUCCU

2881 GGCAUGCUGA AGACAUUGGC ACACUCUGGU AUUCUAGACC UUGGCUCAGA GCUGCCUUUA

2941 CUAGGAUACU GUCACUUAGC AAAAGAAUGG GAUGGAGCCU CAGAUGUGGA GUGACACCAU

3001 CUUCCAAGAA GGAAAGGGUG CCAGGGUCUG GGAUGAAAGC CCUUUGGUGC UAUGUUGGGC

3061 AAGGGCGAGU GCCAGCAAGG GGUUAUUUGC UUGCUCUCUC CAUCAGUGAU GAGGUUCCAU

3121 UUGGUCACAA GAAAUUCACC CCAAUUGCUG AAACAGAGGC UGACUAUUGG CUUAUAGGCA

3181 UGAAACCCCA CUCCCCUCCA CUUCAGGCUG GCUAGAUUAA AAGCUCAGAC CUGUGAAAAA

3241 AAAAAAAA
```

Polynucleotides suitable for use in the present invention also include the following:

Stabilized 6 bp hhRz Sequences

Rho 725
(SEQ ID NO: 3)
5'-UGAAGUG CUGAUGAGCGGUCUUCGGACCGCGAA ACCUCGU-3'

Rho 731
(SEQ ID NO: 4)
5'-GGAUGGU CUGAUGAGCGGUCUUCGGACCGCGAA AAGUGGA-3'

Rho 266
(SEQ ID NO: 5)
5'-AGAGCGU CUGAUGAGCGGUCUUCGGACCGCGAA AGGAAGU-3'

Classical 4 bp HH16 hhRz Sequences

Rho 725-HH16
(SEQ ID NO: 6)
5'-UGAAGUG CUGAUGAGGCCGAAAGGCCGAA ACCUCGU-3'

Rho 731-HH16
(SEQ ID NO: 7)
5'-GGAUGGU CUGAUGAGGCCGAAAGGCCGAA AAGUGGA-3'

Rho 266-HH16
(SEQ ID NO: 8)
5'-AGAGCGU CUGAUGAGGCCGAAAGGCCGAA AGGAAGU-3'

Mini 2 bp hhRz Sequences

Rho 725-mini
(SEQ ID NO: 9)
5'-UGAAGUG CUGAUGAGCUUUUGCGAA ACCUCGU-3'

Rho 731-mini
(SEQ ID NO: 10)
5'-GGAUGGU CUGAUGAGCUUUUGCGAA AAGUGGA-3'

Rho 266-mini
(SEQ ID NO: 11)
5'-AGAGCGU CUGAUGAGCUUUUGCGAA AGGAAGU-3'

Tertiary Modified hhRz Sequences/SM1 (*Schistosoma Mansoni* Tertiary Elements)

Rho 725-SM1
(SEQ ID NO: 12)
5'-UGGU GUAC GAAGUG CUGAUGAGUCCCAAAUAGGACGAA ACCUC-3

Rho 731-SM1
(SEQ ID NO: 13)
5'-UGGG GUAC GAUGGU CUGAUGAGUCCCAAAUAGGACGAA AAGUG-3

Rho 266-SM1
(SEQ ID NO: 14)
5'-CGUA GUAC GAGCGU CUGAUGAGUCCCAAAUAGGACGAA AGGAA-3'

RzB (Peach Latent Mosaic Viroid (PLMVD) Tertiary Elements)

Rho 725-RzB
(SEQ ID NO: 15)
5'-UGGUG UAA AAGUG CUGAUGAGUCGCUGGGAUGCGACGAA ACCUCGU-3'

Rho 731-RzB
(SEQ ID NO: 16)
5'-UGGGG UAA AUGGU CUGAUGAGUCGCUGGGAUGCGACGAA AAGUGGA-3'

Rho 266-RzB
(SEQ ID NO: 17)
5'-CGUAG UAA AGCGU CUGAUGAGUCGCUGGGAUGCGACGAA AGGAAGU-3'

The following sequences comprise hammerhead ribozyme and RNAi target sites for human RHO mRNA A. Hammerhead Ribozyme Human RHO 725 GUC↓ Target Site and hhRz Sequence 1) GUCs↓ 725 Target Sequence in Human RHO: 5'-UCGUGGUC↓CACUUCA-3' (SEQ ID NO:18)
The "C" of GUC↓ is position 725 in the human RHO mRNA sequence.
2) The 725 GUC↓ hhRz sequence is as follows:

(SEQ ID NO: 19***)
3'-<u>AGCACCAAAGCCGGAAAGCCGGAGUAGUC</u><u>GUGAAGU</u>-5'

Use this in SEQ ID for 5'-6' Direction (SEQ ID NO: 19)
<u>UGAAGUGCUGAUGAGGCCGAAAGGCCG</u><u>AAACCACGA</u>

The underlined antisense (in 2) flank sequences anneal to the respective underlined regions of the target sequence listed above (in 1). The center region of the hhRz sequence that is between the underlined antisense sequences is the core catalytic enzyme and Stem II (HH16). The hhRz RNA is written from the 3' to the 5' position in the way that it would anneal to the target sequence in RHO.

B. shRNA (RNAi) 725 Human RHO Target Site and shRNA Sequence:

1. Rhoi725 Target sequence in Human RHO is as follows:

(SEQ ID NO: 20)
5'-UGUUCGUGGUCCACUUCAC-3'

Figure 9:
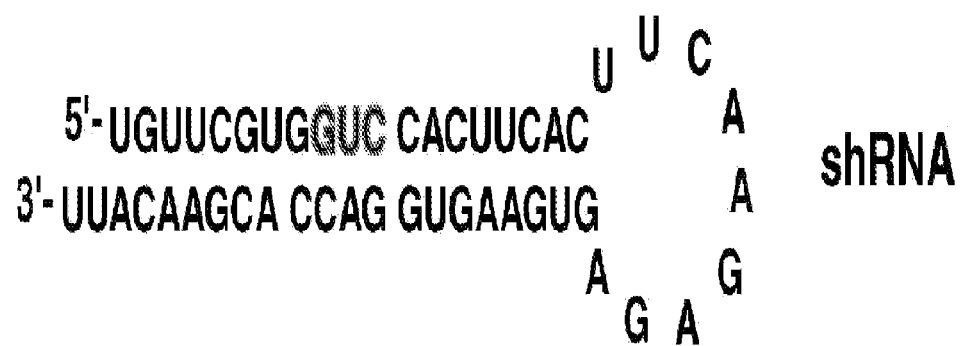
FIG. 9 provides shRNA that targets human RHO mRNA. This sequence forms an shRNA hairpin to attack Human RHO 725 site.

This sequence forms an shRNA hairpin (FIG. 9) to attack Human RHO 725 site. This shRNA was expressed from an H1 promoter in pSUPER vector (OligoEngine). The sequence shown in FIG. 9 is SEQ ID NO:21.

The sequence of human RPE65 mRNA is as follows. Sequences shown in bold and italics represent RPE65 shRNA targets identified according to the invention. Novel shRNAs that attack these target sequences are presented in FIGS. 5-8.

(SEQ ID NO: 22)

```
   1 UCCUUCUUCAUUCUGCAGUUGGUGCCAGAACUCUGGAUCCUGAACUGGAAGAAAAUGUCU
  61 AUCCAGGUUGAGCAUCCUGCUGGUGGUUACAAGAAACUGUUUGAAACUGUGGAGGAACUG
 121 UCCUCGCCGCUCACAGCUCAUGUAACAGGCAGGAUCCCCCUCUGGCUCACCGGCAGUCUC
 181 CUUCGAUGUGGGCCAGGACUCUUUGAAGUUGGAUCUGAGC***CAUUUUACCACCUGUUUGA***U
 241 GGGCAAGCCCUCCUGCACAAGUUUGACUUUAAAGAAGGACAUGUCACAUACCACAGAAGG
 301 UUCAUCCGCACUGAUGCUUACGUACGGGCAAUGACUGAGAAAAGGAUCGUCAUAACAGAA
 361 UUUGGCACCUGUGCUUUCCCAGAUCCCUGCAAGAAUAUAUUUUCCAGGUUUUUUUCUUAC
 421 UUUCGAGGAGUAGAGGUUACUGACAAUGCCCUUGUUAAUGUCUACCCAGUGGGGAAGAU
 481 UACUACGCUUGCACAGAGACCAACUUUAUUACAAAGAUU***AAUCCAGAGACCUUGGAGA***CA
 541 AUUAAGCAGGUUGAUCUUUGCAACUAUGUCUCUGUCAAUGGGCCACUGCUCACCCCCAC
 601 AUUGAAAAUGAUGGAACCGUUUACAAUAUGGUAAUUGCUUUGGAAAAAAUUUUUCAAUU
 661 GCCUACAACAUUGUAAAGAUCCCACCACUGCAAGCAGACAAGGAAGAUCCAAUAAGCAAG
 721 UCAGAGAUCGUUGUACAAUUCCCCUGCAGUGACCGAUUCAAGCCAUCUUACGUUCAUAGU
 781 UUUGGUCUGACUCCCAACUAUAUCGUUUUUGUGGGAGACACCAGUCAAAAUUAACCUGUUC
 841 AAGUUCCUUUCUUCAUGGAGUCUUUGGGGAGCCAACUACAUGGAUUGUUUUGAGUCCAAU
 901 GAAACCAUGGGGGUUUGGCUUCAUAUUGCUGA***CAAAAAAAGGAAAAAGUAC***CUCAAUAAU
 961 AAAUACAGAACUUCUCCUUUCAACCUCUUCCAUCACAUCAACACCUAUGAAGACAAUGGG
1021 UUUCUGAUUGUGGAUCUCUGCUGCUGGAAAGGAUUUGAGUUUGUUUAUAAUUACUUAUAU
1081 UUAGCCAAUUUACGUGAGAACUGGGAAGAGGUGAAAAAAAAUGCCAGAAAGGCUCCCCAA
1141 CCUGAAGUUAGGAGAUAUGUACUUCCUUUGAAUAUUGACAAGGCUGACACAGGCAAGAAU
1201 UUAGUCACGCUCCCCAAUACAACUGCCACUGCAAUUCUGUGCAGUGACGAGACUAUCUGG
1261 CUGGAGCCUGAAGUUCUCUUUUCAGGGCCUCGUCAAGCAUUUGAGUUUCCUCAAAUCAAU
1321 UACCAGAAGUAUUGUGGGAAACCUUACACAUAUGCGUAUGGACUUGGCUUGAAUCACUUU
1381 GUUCCAGAUAGGCUCUGUAAGCUGAAUGUCAAAACUAAAGAAACUUGGGUUUGGCAAGAG
1441 CCUGAUUCAUACCCAUCAGAACCCAUCUUUGUUUCUCACCCAGAUGCCUUGGAAGAAGAU
1501 GAUGGUGUAGUUCUGAGUGUGGUGGUGAGCCCAGGAGCAGGACAAAAGCCUGCUUAUCUC
1561 CUGAUUCUGAAUGCCAAGGACUUAAGUGAAGUUGCCCGGGCUGAAGUGGAGAUUAACAUC
```

```
                                                -continued
1621 CCUGUCACCUUUCAUGGACUGUUCAAAAAAUCUUGAGCAUACUCCAGCAAGAUAUGUUUU

1681 UGGUAGCAAAACUGAGAAAAUCAGCUUCAGGUCUGCAAUCAAAUUCUGUUCAAUUUUAGC

1741 CUGCUAUAUGUCAUGGUUUUAACUUGCAGAUGCGCACAAUUUUGCAAUGUUUUACAGAAA

1801 GCACUGAGUUGAGCAAGCAAUUCCUUUAUUUAAAAAAAAAAGUACGUAUUUAGAUAAUCA

1861 UACUUCCUCUGUGAGACAGGCCAUAACUGAAAACUCUUAAAUAUUUAGCAAUCAAAUAG

1921 GAAAUGAAUGUGGACUUACUAAAUGGCUUUUAAUUCCUAUUAUAAGAGCAUAUUUUAGGU

1981 ACCUAUCUGCUCCAAUUAUAUUUUAACAUUUAAAAACCAAAGUCCUCUACACUUGAUUU

2041 AUAUUAUAUGUGGCUUUGCUGAGUCAAGGAAGUAUCAUGCAAUAAGGCUUAAUUACUAAA

2101 UGUCAAACCAAACUUUUUCUCAAACCAGGGACUAUCAUCUAAGAUUAAUUACAGUAAUUA

2161 UUUUGCGUAUACGUAACUGCUCAAAGAUUAUGAAUCUUAUGAAUGUUAACCUUUCCGUUU

2221 AUUACAAGCAAGUACUAUUAUUUCUGAUUUUAUAAUAAGAAAAUCUGUGUUUAAUCAACU

2281 GAGGCCUCUCAACCAAAUAACAUCUCAGAGAUUAAGUUAUAUAUUAAAAGCUUAUGUAAC

2341 AUAAAAGCAAGUACAUAUAGUAGUGACUAUAUUUAAAAAAACAGCAUAAAAUGCUUAAAA

2401 AUGUAAUAUUUACUAAAAUCAGAUUAUGGGAUAAUGUUGCAGGAUUAUACUUUAUUGCAU

2461 CUUUUUUGUUUAAUUGUAUUUAAGCAUUGUGCAAUCACUUGGGAAAAAUAUUAAAUUAUU

2521 AACAUUGAGGUAUUAAUACAUUUUAAGCCUUUUGUUUUUAAAUUUCUUUUCUUCCAGAGA

2581 UUGUUUAAAAAUAAAUAUUGACAAAAAU
```

Mouse RPE65 mRNA has the following sequence:

```
                                                                (SEQ ID NO: 23)
   1 UCCUCAUCCU ACAGCUGGUA CCAGAACUCU CUCUAAUCUU CACUGGAAGA AAUGUCUAU

61 CCAAAUUGAA CACCCUGCUG GUGGCUACAA GAAACUAUUU GAAACUGUGG AGGAACUGUC

121 CUCACCACUA ACAGCUCAUG UCACAGGCAG GAUUCCCCUC UGGCUCACUG GCAGUCUCCU

181 CCGAUGUGGG CCAGGGCUCU UUGAAGUUGG AUCUGAGCCU UUCUAUCACC UGUUUGAUGG

241 ACAAGCCCUU UUGCACAAGU UUGACUUCAA GGAGGGCCAU GUCACAUACC ACAGAAGAUU

301 CAUCCGCACU GAUGCUUAUG UUCGAGCAAU GACUGAGAAG AGGAUUGUCA UAACAGAAUU

361 UGGCACCUGU GCUUUCCCAG ACCCCUGCAA GAAUAUAUUU UCCAGGUUUU UUCUUACUU

421 UAAAGGAGUA GAGGUUACUG ACAAUGCCCU UGUAAAUAUC UACCCAGUGG GAGAAGAUUA

481 CUAUGCAUGC ACAGAGACCA ACUUUAUCAC AAAGAUUAAC CCAGAGACCU GGAGACAAU

541 UAAGCAGGUU GAUCUUUGCA ACUAUAUUUC UGUCAAUGGU GCCACUGCUC AUCCACAUAU

601 UGAAAGUGAU GGAACAGUUU ACAACAUUGG GAAUUGCUUU GGAAAAAAUU UUACAGUUGC

661 CUACAACAUU AUUAAGAUCC CUCCACUGAA AGCAGACAAG GAAGAUCCAA UAAACAAGUC

721 AGAAGUUGUU GUGCAGUUCC CCUGCAGUGA UCGUUUCAAG CCAUCUUAUG UACACAGUUU

781 UGGUCUGACU CCCAACUAUA UCGUUUUUGU GGAGACUCCA GUCAAAAUUA ACCUUUUCAA

841 GUUUCUUUCU UCGUGGAGUC UUUGGGGAGC CAACUACAUG GACUGUUUCG AGUCCAAUGA

901 AAGCAUGGGG GUUGGCUUC AUGUUGCUGA UAAAAAAGA AGAAAUACU UCAAUAACAA

961 AUACAGGACU UCCCCUUUCA AUCUCUUCCA UCAUAUCAAU ACUUAUGAAG ACAAUGGAUU

1021 UCUGAUUGUG GAUCUCUGUU GCUGGAAAGG GUUUGAAUUU GUUUAUAAUU ACUUAUAUUU

1081 AGCCAAUUUA CGUGAGAAUU GGGAAGAAGU UAAAGAAAU GCUAUGAAGG CUCCUCAGCC

1141 UGAAGUCAGG AGAUAUGUAC UUCCUUUGAC AAUUGACAAG GUCGACACAG GCAGAAAUUU

1201 AGUCACACUG CCCCAUACAA CUGCCACAGC CACUCUGCGC AGUGAUGAGA CCAUAUGGCU
```

-continued

```
1261 GGAACCUGAG GUUCUCUUUU CAGGGCCUCG UCAAGCCUUU GAAUUUCCUC AAAUCAAUUA

1321 CCAGAAAUUU GGAGGGAAAC CUUAUACUUA UGCAUACGGA CUUGGGUUGA AUCACUUUGU

1381 UCCUGACAAG CUCUGUAAGA UGAACGUCAA AACUAAAGAA AUCUGGAUGU GGCAAGAGCC

1441 AGAUUCUUAC CCAUCUGAAC CCAUCUUUGU UUCUCAACCA GAUGCUCUGG AAGAAGAUGA

1501 UGGUGUGGUU CUGAGUGUGG UGGUGAGCCC UGGGGCAGGG CAAAAGCCUG CAUAUCUCCU

1561 GGUUCUGAAU GCCAAAGACU UGAGUGAAAU UGCCAGGGCU GAAGUGGAGA CUAAUAUCCC

1621 UGUGACCUUC CAUGGACUGU UCAAAAGAUC CUGAACAUAU UCCAGAGAUG GCUCAGCAGU

1681 ACAACACUGA CUGCCCUUCU ACAGAUCGUG UGUUCAAUUC CCAAAGAUCA CCUGGUGACU

1741 CACUUCCAUC UGAGACGGAA UCCAAUGCCC UCUUAUGCUG UUUCUGAAGA CAGCAAAAGU

1801 GUACUCAUAU AUACAUAUGA UAAAUAAAUC UUUAAAAAAA ACAAAAAAAA AAAAAAAAA

1861 AA
```

FIG. 4 provides mouse RPE65 Hammerhead Ribozyme Sequences identified in performance of the present invention.

FIGS. 5-8 provide shRNAs that target human RPE65.

Figure 2A:
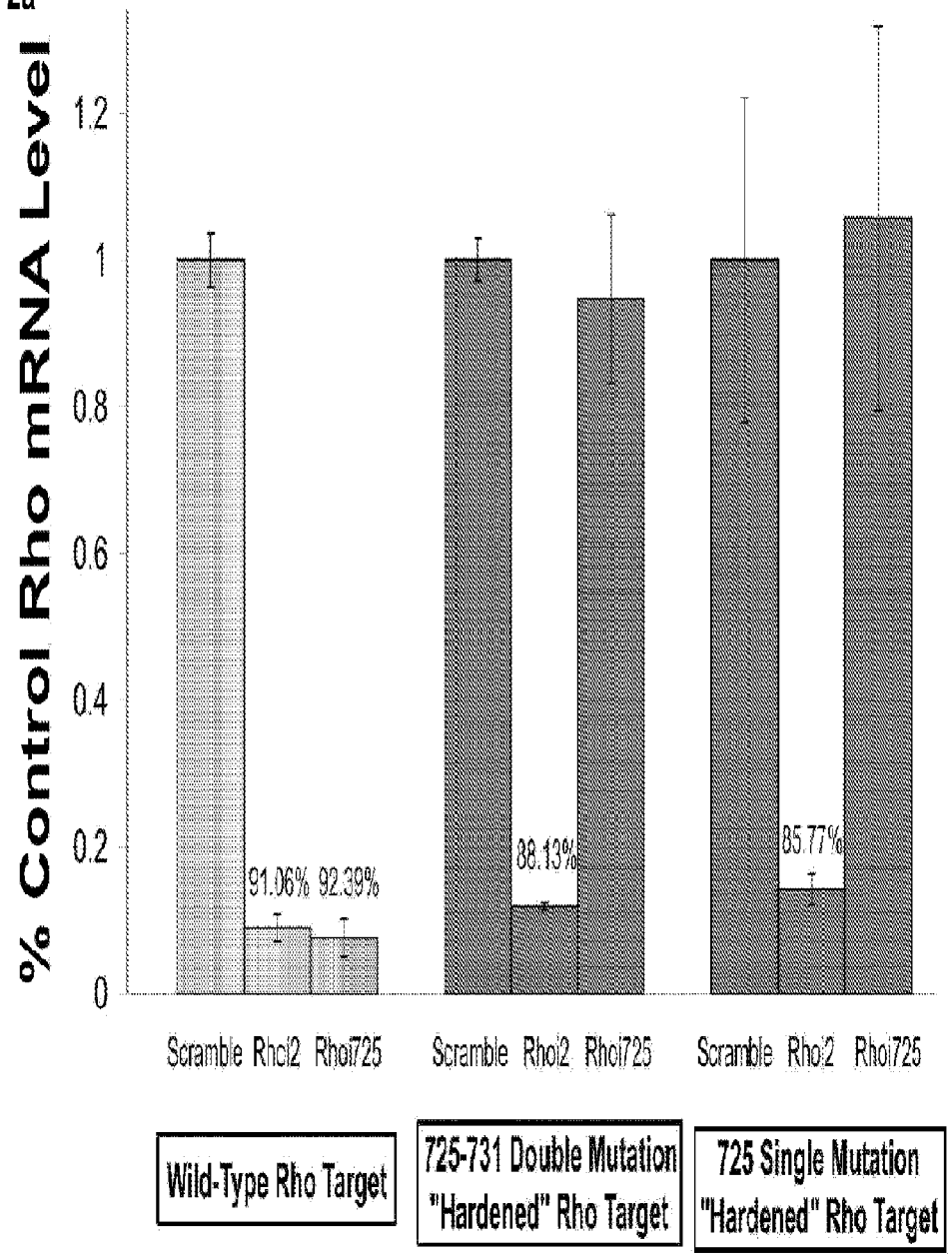
FIGS. 2a and 2b provides data evidencing effective shRNA Knockdown of RHO expression. a) shRNA construct targeted to 725 site (Rhoi725) was compared to a known successful shRNA construct (Rhoi2 from Cashman et. al. 2005) using qRT-PCR. Full-length Rho constructs with single and double mutation(s) in the target site showed significant resistance to Rhoi725 indicating specificity of cleavage site. b) Knockdown observations were confirmed at the protein level (western blot).
Figure 2B:
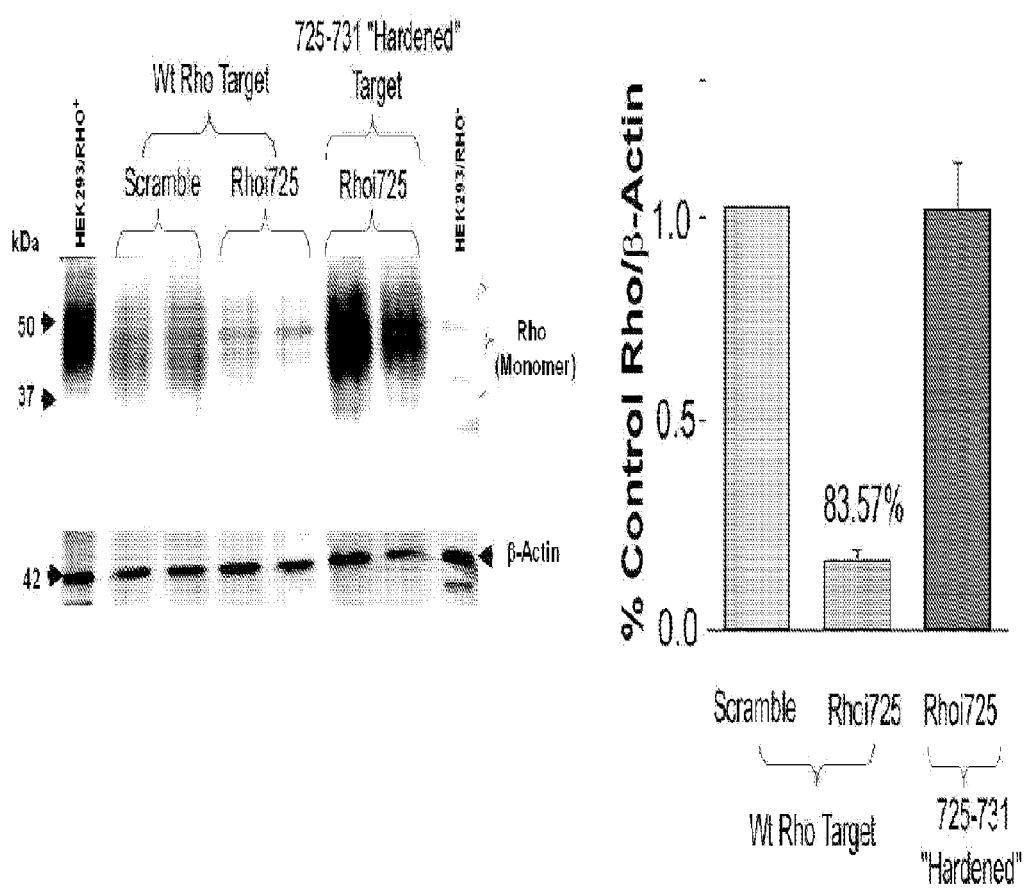

In general, the foregoing HhRz and shRNA polynucleotides capable of facilitating a reduction in RHO or RPE65 target mRNA were developed against accessible regions of RHO and RPE65 mRNA regions we identified using a variety of techniques. In particular, full length mRNAs for human RHO mRNA, and human and mouse RPE65 mRNAs were archived from GenBank. RNA secondary structure folding was conducted with MFold (vers. 3.2), SFold and OligoWalk algorithm (RNAStructure, vers 4.5, Mathews, 1999, 2006). Independent sampling outputs were convolved into a final statistical predictor of accessibility which we call multiparameter prediction of RNA accessibility (mppRNA). Local regional accessibility was compared statistically between the human and mouse RHO targets for the different algorithms by parametric t-tests at standard criterion significance ($p<0.05$). Transfection experiments evaluating knockdown by shRNA and ribozyme vectors and controls were subject to one-way ANOVA to evaluate the null hypothesis of equivalent means. Post-hoc t-tests were used to evaluate differences between samples and controls and between samples.

hhRz were expressed within an engineered adenoviral VAI chimera RNA. HhRzs against accessible and inaccessible regions were tested in a 96-well screening assay where the target was the dicistronic mRNA, RHO-IRES-SEAP, that expressed both RHO and SEAP proteins (HEK293S-RHO-IRES-SEAP cells). SEAP is secreted from live cells and measured in a fluorescence enzyme assay. shRNAs were cloned into pSUPER (Oligoengine). Maximum knockdown in this assay is expected at 50%. A range of knockdown efficacies were identified. The most efficient hhRz was a polynucleotide targeting the 725 GUC site. The most potent PTGS agent is an shRNA which suppresses 92% of RHO mRNA and 83% of RHO protein (see FIGS. 1 and 2a and 2b). There are substantial differences between the mean KD (knock-down) levels by hhRzs targeting common accessible regions (e.g. the 250 region embracing 250, 257, 263, 266, 272, 274; 725 region embracing 725, 730, 731, 737). HhRzs targeting inaccessible sites (control) (e.g. hhRz GUC↓, 785) exerted no KD. Three hhRzs promoted the greatest amount of SEAP protein KD from the RHO-IRES-SEAP dicistronic expressing cell line (266, 725, 731).

Figure 3:
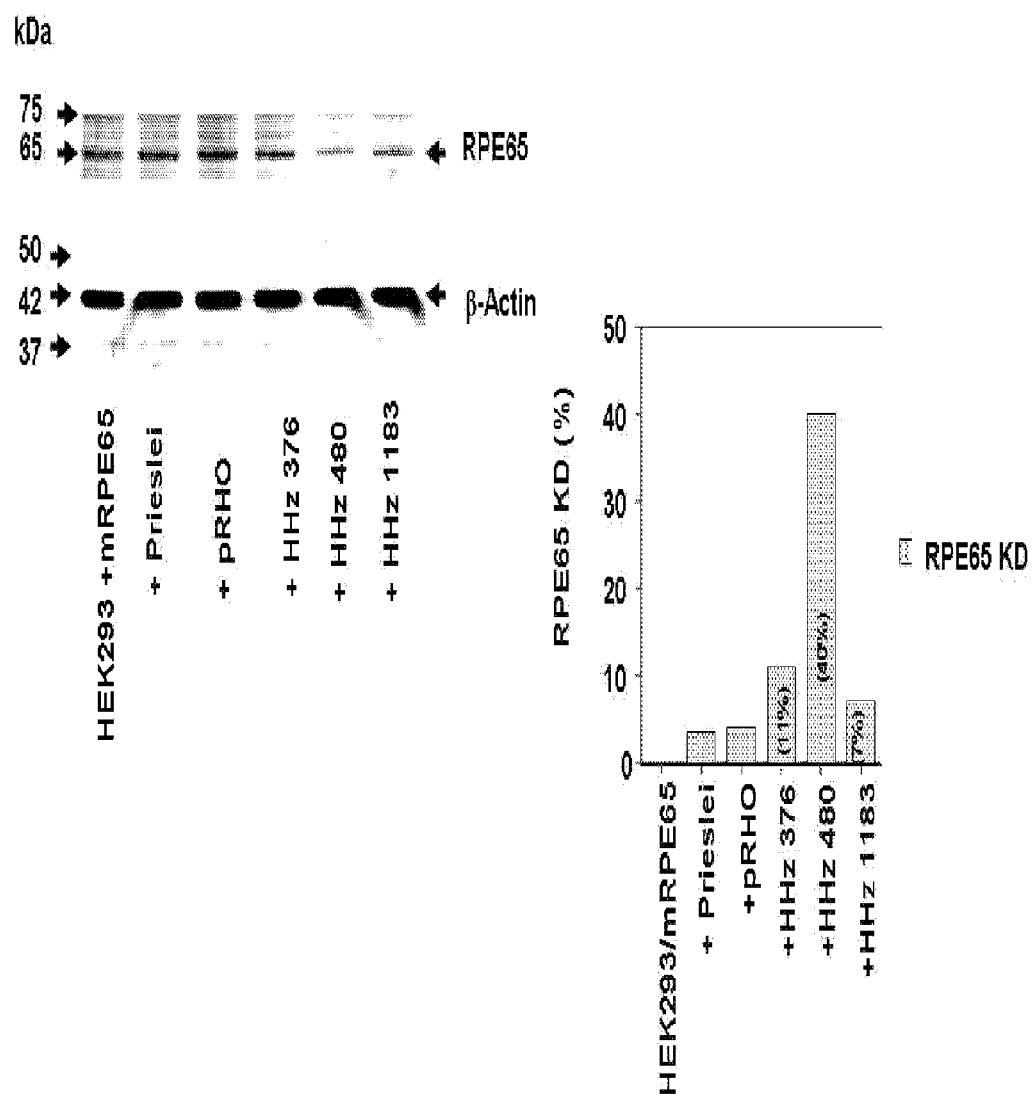
FIG. 3. provides data obtained from evaluation of RPE65 knockdown using hhRz Data were obtained from western blots of protein encoded by RPE65 mRNA and quantitation of the protein.
Figure 5:
FIG. 5 provides a description of an shRNA that targets human RPE65 at site 221 (human RPE65 221 shRNA).

In separate studies, accessible regions in mouse RPE65 mRNA were predicted, and hhRz were constructed and tested using cotransfection of a VAI-hhRz expression plasmid and RPE65 expression construct in HEK293S cells (FIG. 3).

For cell culture and transfection, suspension adapted Human Embryonic Kidney cells (HEK-293S) were maintained in Dulbecco's Modified Eagle's Medium/F-12 nutrient mix (DMEM/F12) with 10% (v/v) heat inactivated calf serum and antibiotics. In transient transfections cells in 24 well plates were co-transfected (Lipofectamine 2000, InVitrogen) with 150 ng of CMV expression plasmids for human RHO or mouse RHO, and 5 µg of shRNA or hammerhead ribozyme expression plasmids per well. Control ribozyme vectors had a nonspecific adapter in place of the ribozyme sequence and control shRNA vectors had an irrelevant scrambled sequence. After 48 hrs cells were harvested, total RNA was purified (RNAeasy, Qiagen), and first strand cDNA was synthesized, or cells were extracted for western analysis.

For SEAP Assays: 50 µL of conditioned cell culture media was transferred to separate wells in black-walled 96 well plates and incubated at 65° C. for 30 minutes. After cooling samples to room temp., 45 µL of Diethanolamine Assay Buffer (pH 9.8, 2 mM $MgCl_2$, 1 mM L-Homoarginine) was added per well. 5 µL of 4-methyl umbelliferyl phosphate (4-MUP) fluorescent substrate was added to each well for a final concentration of 0.04 mM per well, and fluorescence (480 nm excitation/530 nm emission) assayed on a Fluoroskan FL plate reader after incubating for 55 minutes at room temperature in the dark.

For Real-Time Quantitative RT-PCR, total RNA was purified from transfected cells with RNeasy kit (Qiagen) and treated with TURBO DNase (Ambion). cDNA synthesis was performed using 500 ng of total RNA with the AffinityScript Reverse Transcriptase system (Stratagene) using the supplied oligo(dT) primers. Quantitative PCR for human Rho mRNA was performed in a Smart Cycler II (Cepheid) thermocycler. Primers that spanned adjacent exons and a probe primer containing FITC at the 5' end and a quenching dye at the 3' end were designed using primer quest software (IDT).

For quantitative analysis, transfection experiments evaluating knockdown by shRNA and ribozyme vectors and controls were subject to one-way ANOVA to evaluate the null hypothesis of equivalent means. Post-hoc t-tests were used to evaluate differences between samples and controls and between samples.

While the invention has been illustrated by specific working embodiments, those skilled in the art will recognize that minor modifications can be made without deviating from the spirit of the invention.

I claim:

1. A composition comprising a polynucleotide, wherein the polynucleotide comprises the sequence of SEQ ID NO:21, SEQ ID NO:30, or SEQ ID NO:31.

2. The composition of claim 1, wherein the polynucleotide comprises the sequence of SEQ ID NO:21.

3. The composition of claim 1, wherein the polynucleotide comprises the sequence of SEQ ID NO:30.

4. The composition of claim 1, wherein the polynucleotide comprises the sequence of SEQ ID NO:31.

* * * * *

SEQUENCE LISTING

<160> NUMBER OF SEQ ID NOS: 33

<210> SEQ ID NO 1
<211> LENGTH: 1532
<212> TYPE: RNA
<213> ORGANISM: Homo sapiens

<400> SEQUENCE: 1

| | | | | | |
|---|---|---|---|---|---|
| agagucaucc | agcuggagcc | cugaguggcu | gagcucaggc | cuucgcagca | uucuugggug | 60 |
| ggagcagcca | cgggucagcc | acaagggcca | cagccaugaa | uggcacagaa | ggcccuaacu | 120 |
| ucuacgugcc | cuucuccaau | gcgacggug | ugguacgcag | ccccuucgag | uacccacagu | 180 |
| acuaccuggc | ugagccaugg | caguucucca | ugcuggccgc | cuacauguuu | cugcugaucg | 240 |
| ugcugggcuu | ccccaucaac | uuccucacgc | ucuacgucac | cguccagcac | aagaagcugc | 300 |
| gcacgccucu | caacuacauc | cugcucaacc | uagccguggc | ugaccucuuc | augguccuag | 360 |
| guggcuucac | cagcacccuc | uacaccucuc | ugcauggaua | cuucgucuuc | gggcccacag | 420 |
| gaugcaauuu | ggagggcuuc | uuugccaccc | ugggcgguga | aauugcccug | uggccuugg | 480 |
| ugguccuggc | caucgagcgg | uacguggugg | uguaagcc | caugagcaac | uuccgcuucg | 540 |
| gggagaacca | ugccaucaug | ggcguugccu | ucaccugggu | cauggcgcug | gccugcgccg | 600 |
| cacccccacu | cgccggcugg | uccagguaca | uccccgaggg | ccugcagugc | ucguguggaa | 660 |
| ucgacuacua | cacgcucaag | ccggagguca | caacgaguc | uuuugucauc | uacauguucg | 720 |
| ugguccacuu | caccaucccc | augauuauca | ucuuuuucug | cuauggggcag | cucgucuuca | 780 |
| ccgucaagga | ggccgcugcc | cagcagcagg | agucagccac | cacacagaag | gcagagaagg | 840 |
| aggucacccg | cauggucauc | aucaugguca | ucgcuuccu | gaucgcuggg | gugcccuacg | 900 |
| ccagcguggc | auucuacauc | uucacccacc | agggcuccaa | cuucggucc | aucuucauga | 960 |
| ccaucccagc | guucuuugcc | aagagcgccg | ccaucuacaa | cccugucauc | uauaucauga | 1020 |
| ugaacaagca | guuccggaac | ugcaugcuca | ccaccaucug | cugcggcaag | aacccacugg | 1080 |
| gugacgauga | ggccucugcu | accgugucca | agacggagac | gagccaggug | gccccggccu | 1140 |
| aagaccugcc | uaggacucug | uggccgacua | uaggcgucuc | ccaucccua | caccuucccc | 1200 |
| cagccacagc | caucccacca | ggagcagcgc | cugugcagaa | ugaacgaagu | cacauaggcu | 1260 |
| ccuuaauuuu | uuuuuuuuu | uuaagaaaua | auuaaugagg | cuccucacuc | accugggaca | 1320 |
| gccugagaag | ggacauccac | caagaccuac | ugaucuggag | uccacguuc | cccaaggcca | 1380 |
| gcgggaugug | ugccccuccu | ccucccaacu | caucuuucag | gaacacgagg | auucuugcuu | 1440 |
| ucuggaaaag | ugucccagcu | uagggauaag | ugucuagcac | agaaugggc | acacaguagg | 1500 |
| ugcuuaauaa | augcuggaug | gaugcaggaa | gg | | | 1532 |

<210> SEQ ID NO 2
<211> LENGTH: 3249
<212> TYPE: RNA
<213> ORGANISM: Mouse

<400> SEQUENCE: 2

| | | | | | |
|---|---|---|---|---|---|
| cgucaguggc | ugagcucgcc | aagcagccuu | ggucucuguc | uacgaagagc | ccguggggca | 60 |
| gccucgagag | ccgcagccau | gaacggcaca | gagggcccca | auuuuuaugu | gcccuucucc | 120 |
| aacgucacag | gcguggugcg | gagcccuuc | gagcagccgc | aguacuaccu | ggcggaacca | 180 |
| uggcaguucu | ccaugcuggc | agcguacaug | uuccugcuca | ucgugcuggg | cuuccccauc | 240 |

| | |
|---|---|
| aacuuccuca cgcucuacgu caccguacag cacaagaagc ugcgcacacc ccucaacuac | 300 |
| auccugcuca acuuggccgu ggcugaccuc uucauggucu ucggaggauu caccaccacc | 360 |
| cucuacacau cacuccaugg cuacuucguc uuugggccca caggcuguaa ucucgagggc | 420 |
| uucuuugcca cacuuggagg ugaaaucgcc cugugguccc ugguggnccu ggccauugag | 480 |
| cgcuacgugg uggucugcaa gccgaugagc aacuuccgcu ucggggagaa ucacgcuauc | 540 |
| auggugugug ucuucaccug gaucauggcg uuggccugug cugcuccccc acucguuggc | 600 |
| ugguccaggu acaucccuga gggcaugcaa uguucaugcg ggauugacua cuacacacuc | 660 |
| aagccugagg ucaacaacga auccuuuguc aucuacaugu cguggucca cuucaccauu | 720 |
| ccuaugaucg ucaucuucuu cugcuauggg cagcuggucu ucacagucaa ggaggcggcu | 780 |
| gcccagcagc aggagucagc caccacucag aaggcagaga aggaagucac ccgcaugguu | 840 |
| aucaucaugg ucaucuucuu ccugaucugc uggcuucccu acgccagugu ggccuucuac | 900 |
| aucuucaccc accagggcuc caacuucggc cccaucuuca ugacucugcc agcuuucuuu | 960 |
| gcuaagagcu cuuccaucua uaacccgguc aucuacauca uguugaacaa gcaguuccgg | 1020 |
| aacuguaugc ucaccacgcu gugcugcggc aagaauccac uggagaugac cgacgccucu | 1080 |
| gccaccgcuu ccaagacgga gaccagccag guggcuccag ccuaagccug ccagagacu | 1140 |
| guggcugaaa guaggagucu ccuguccca cacaccccag ccacagcccc caccaggagc | 1200 |
| agcacccguu gggaugaggu caugcaggcu cccucagugu ucuuucuuu guuuuuaaug | 1260 |
| aauucaugaa agcaaaauga ggcuccccac ucaauggggga cagcuugaca aagggcaucc | 1320 |
| auccaccaag accauccuca accuggaguc cccaauuccc gggggccag cgggaucugu | 1380 |
| accccucccu cagcuugucu aucaggaaca ugacaagugu cccggcuuag ggcuaaaugu | 1440 |
| cuaggacaga auggaacaca uaguagcuga uuaauaaaug cuagcuggau gaagggagga | 1500 |
| augagugacu gacugagugg auauaugagu gaagggauua auggaaggga acauggaugu | 1560 |
| ccucaggugc ccaaccuggc agauccaguc augucuggcu ggaaucuaua agcaguuuua | 1620 |
| cauaccugcc cugguuuucu cugcccccac ccccacccca guuggaucuc ccaaauccag | 1680 |
| ggcccugaua gaauauggcu gcuucaaaga cagagagaug aggggaggga ggggggaggg | 1740 |
| agagagggag ggagggagac acagagaggg aauaugugug augcgugugu auguguguau | 1800 |
| gugugugugu aaacacuuug uauauaaaga guacagcugg uaguuauguu acaaguaaca | 1860 |
| ccgacuaaua uaauuaauua accauccuaa uggucucugc uguuagunga cugcuuggga | 1920 |
| auuaggcagg gcccaagcac ucagauaagg uauuucccuc agccagagua ggcuuugca | 1980 |
| aaugacccag gccuucaggc cugugcaggg cuagagcugg auuacagaga uaaaugacag | 2040 |
| ugacagcaac gugagcugca gcccuuagga cugagaaagc aucgagacca ggggucuccg | 2100 |
| gcaaggccua ggucucccu ucaguaugga aaccuugccu caugucucuc agccuccuug | 2160 |
| gccguggag auccagcccu uccucuuggc uucuggauac auuugcucuu cuacaccagc | 2220 |
| aaccaagugg caacaguucc aggccaguau ggaguuuuag aagccaugcc aauaugccca | 2280 |
| ccuucaggga gcagcugagu ccuugaugcc acccuuguuc ugaagaguuc agaaacacag | 2340 |
| ugcaagacau gaccaggccu caaccuuagg augcucaugg auccaguucu uagcucccuu | 2400 |
| guuggauaug cuguuuuccu uggccuuugg ucuuuucuuu aucccagagg guuuggcuu | 2460 |
| uaaggccaac aggaacuaug ggguaccaga auugagcagc cucagcucgc auccucccuc | 2520 |
| uauagaacca cagcgggcc cucagcaggc ccaacucugc auggggacag aggcauuaaa | 2580 |
| agcucagcuc cuacacuugg uggcaguggu ggucuguugc ucucaagcuc uuucaaaaug | 2640 |

```
gauggaaacu gggacgcuuc ccugaccccu gguuaugaaa gacuagacug ugugggaca    2700 aacaguccag aguccggggg aaugugauag agcagcucca ucauuuuuag aaacccaauu    2760
ugaggcagua uagagaugug ugaccucua uaagccucug uaucugcaaa gaggagcuua     2820
gaccugcccu ugaggggauu auaugagauu uaagggacuu auguggccag ccuacuuccu    2880
ggcaugcuga agacauuggc acacucuggu auucuagacc uuggcucaga gcugccuuua    2940
cuaggauacu gucacuuagc aaaagaaugg gauggagccu cagaguggga ugacaccau     3000 cuuccaagaa ggaaggggug ccagggucug ggaugaaagc ccuuggugc uauguugggc     3060 aagggcgagu gccagcaagg gguuauuugc ugcucucuc caucagugau gagguuccau     3120
uuggucacaa gaaauucacc ccaauugcug aaacagaggc ugacuauugg cuuauaggca    3180
ugaaacccca cuccccucca cuucaggcug gcuagauuaa aagcucagac cugugaaaaa    3240
aaaaaaaaa                                                            3249
```

<210> SEQ ID NO 3
<211> LENGTH: 40
<212> TYPE: RNA
<213> ORGANISM: artificial sequence
<220> FEATURE:
<223> OTHER INFORMATION: Rho 725 hhRz

<400> SEQUENCE: 3
ugaagugcug augagcgguc uucggaccgc gaaaccucgu                          40

<210> SEQ ID NO 4
<211> LENGTH: 40
<212> TYPE: RNA
<213> ORGANISM: artificial sequence
<220> FEATURE:
<223> OTHER INFORMATION: Rho 731 hhRz sequence

<400> SEQUENCE: 4
ggauggucug augagcgguc uucggaccgc gaaaagugga                          40

<210> SEQ ID NO 5
<211> LENGTH: 40
<212> TYPE: RNA
<213> ORGANISM: artificial sequence
<220> FEATURE:
<223> OTHER INFORMATION: Rho 266 hhRz sequence

<400> SEQUENCE: 5
agagcgucug augagcgguc uucggaccgc gaaaggaagu                          40

<210> SEQ ID NO 6
<211> LENGTH: 36
<212> TYPE: RNA
<213> ORGANISM: artificial sequence
<220> FEATURE:
<223> OTHER INFORMATION: Rho 725-HH16 hhRz sequence

<400> SEQUENCE: 6
ugaagugcug augaggccga aaggccgaaa ccucgu                              36

<210> SEQ ID NO 7
<211> LENGTH: 36
<212> TYPE: RNA
<213> ORGANISM: artificial sequence
<220> FEATURE:
<223> OTHER INFORMATION: Rho 731-HH16 sequence

<400> SEQUENCE: 7

```
ggauggucug augaggccga aaggccgaaa agugga                                36

<210> SEQ ID NO 8
<211> LENGTH: 36
<212> TYPE: RNA
<213> ORGANISM: artificial sequence
<220> FEATURE:
<223> OTHER INFORMATION: Rho 266-HH16 sequence

<400> SEQUENCE: 8
agagcgucug augaggccga aaggccgaaa ggaagu                                36

<210> SEQ ID NO 9
<211> LENGTH: 32
<212> TYPE: RNA
<213> ORGANISM: artificial sequence
<220> FEATURE:
<223> OTHER INFORMATION: Rho 725-mini sequence

<400> SEQUENCE: 9
ugaagugcug augagcuuuu gcgaaaccuc gu                                    32

<210> SEQ ID NO 10
<211> LENGTH: 32
<212> TYPE: RNA
<213> ORGANISM: artificial sequence
<220> FEATURE:
<223> OTHER INFORMATION: Rho 731-mini sequence

<400> SEQUENCE: 10
ggauggucug augagcuuuu gcgaaaagug ga                                    32

<210> SEQ ID NO 11
<211> LENGTH: 32
<212> TYPE: RNA
<213> ORGANISM: artificial sequence
<220> FEATURE:
<223> OTHER INFORMATION: Rho 266-mini sequence

<400> SEQUENCE: 11
agagcgucug augagcuuuu gcgaaaggaa gu                                    32

<210> SEQ ID NO 12
<211> LENGTH: 43
<212> TYPE: RNA
<213> ORGANISM: artificial sequence
<220> FEATURE:
<223> OTHER INFORMATION: Rho 725-SM1 sequence

<400> SEQUENCE: 12
ugugugacga agugcugaug aguccccaaau aggacgaaac cuc                        43

<210> SEQ ID NO 13
<211> LENGTH: 43
<212> TYPE: RNA
<213> ORGANISM: artificial sequence
<220> FEATURE:
<223> OTHER INFORMATION: Rho 731-SM1 sequence

<400> SEQUENCE: 13
ugggguacga uggucugaug aguccccaaau aggacgaaaa gug                        43

<210> SEQ ID NO 14
<211> LENGTH: 43
<212> TYPE: RNA
<213> ORGANISM: artificial sequence
<220> FEATURE:
```

<223> OTHER INFORMATION: Rho 266-SM1 sequence

<400> SEQUENCE: 14
cguaguacga gcgucugaug agucccaaau aggacgaaag gaa     43

<210> SEQ ID NO 15
<211> LENGTH: 46
<212> TYPE: RNA
<213> ORGANISM: artificial sequence
<220> FEATURE:
<223> OTHER INFORMATION: Rho 725-RzB sequence

<400> SEQUENCE: 15
ugguguaaaa gugcugauga gucgcuggga ugcgacgaaa ccucgu     46

<210> SEQ ID NO 16
<211> LENGTH: 46
<212> TYPE: RNA
<213> ORGANISM: artificial sequence
<220> FEATURE:
<223> OTHER INFORMATION: Rho 731-RzB5' sequence

<400> SEQUENCE: 16
ugggguaaau ggucugauga gucgcuggga ugcgacgaaa agugga     46

<210> SEQ ID NO 17
<211> LENGTH: 46
<212> TYPE: RNA
<213> ORGANISM: artificial sequence
<220> FEATURE:
<223> OTHER INFORMATION: Rho 266-RzB sequence

<400> SEQUENCE: 17
cguaguaaag cgucugauga gucgcuggga ugcgacgaaa ggaagu     46

<210> SEQ ID NO 18
<211> LENGTH: 15
<212> TYPE: RNA
<213> ORGANISM: Homo sapiens

<400> SEQUENCE: 18
ucguggucca cuuca     15

<210> SEQ ID NO 19
<211> LENGTH: 36
<212> TYPE: RNA
<213> ORGANISM: Homo sapiens

<400> SEQUENCE: 19
ugaagugcug augaggccga aaggccgaaa ccacga     36

<210> SEQ ID NO 20
<211> LENGTH: 19
<212> TYPE: RNA
<213> ORGANISM: Homo sapiens

<400> SEQUENCE: 20
uguucguggu ccacuucac     19

<210> SEQ ID NO 21
<211> LENGTH: 49
<212> TYPE: RNA
<213> ORGANISM: artificial sequence
<220> FEATURE:
<223> OTHER INFORMATION: Human RHO 725 shRNA sequence

<400> SEQUENCE: 21

```
uguucguggu ccacuucacu ucaagagagu gaaguggacc acgaacauu          49
```

<210> SEQ ID NO 22
<211> LENGTH: 2608
<212> TYPE: RNA
<213> ORGANISM: Homo sapiens

<400> SEQUENCE: 22

```
uccuucuuca uucugcaguu ggugccagaa cucuggaucc ugaacuggaa gaaaaugucu    60
auccagguug agcauccugc ugugguuac aagaaacugu ugaaacugu ggaggaacug     120
uccucgccgc ucacagcuca guaacaggc aggaucccc ucuggcucac cggcagucuc     180
cuucgaugug ggccaggacu cuuugaaguu ggaucugagc cauuuuacca ccuguuugau    240
gggcaagccc uccugcacaa guuugacuuu aaagaaggac augucacaua ccacagaagg    300
uucauccgca cugaugcuua cgacgggca augacgaga aaaggaucgu cauaacagaa     360
uuggcaccu gugcuuuccc agaucccugc aagaauauau uuccagguu uuuucuuac      420
uuucgaggag uagagguuac ugacaaugcc cuuguuaaug ucuacccagu gggggaagau    480
uacuacgcuu gcacagagac caacuuuauu acaaagauua uccagagac cuuggagaca    540
auuaagcagg uugaucuuug caacuaugc ucugucaaug gggccacugc ucaccccac     600
auugaaaaug auggaaccgu uuacaauauu gguauugcu uuggaaaaaa uuuucaauu     660
gccuacaaca uuguaaagau cccaccacug caagcagaca aggaagaucc aauaagcaag    720
ucagagaucg uuguacaauu ccccugcagu gaccgauuca agccaucuua cguucauagu    780
uuuggucuga cucccaacua uaucguuuuu guggagacac cagucaaaau uaaccuguuc    840
aaguccuuu cuucauggag ucuuuggga gccaacuaca uggauuguuu ugaguccaau    900
gaaaccaugg ggguugggcu ucauauugcu gacaaaaaaa ggaaaaagua ccucaauaau    960
aaauacagaa cuucuccuuu caaccucuuc caucacauca acaccauga agacaauggg  1020
uuucugauug uggaucucug cugcuggaaa ggauuugagu uuguuauaa uuacuuauau  1080
uuagccaauu uacgugagaa cugggaagag gugaaaaaaa augccagaaa ggcuccccaa  1140
ccugaaguua ggagauaugu acuuccuuug aauauugaca aggcugacac aggcaagaau  1200
uuagucacgc uccccaauac aacugccacu gcaauucugu gcagugacga gacuaucugg  1260
cuggagccug aaguucucuu ucagggccu cgucaagcau ugaguuucc ucaaaucaau  1320
uaccagaagu auuuguggaa accuacacac uaugcguaug gacuuggcuu gaaucacuuu  1380
guuccagaua ggcucuguaa gcugaauguc aaaacuaaag aaacuugggu uggcaagag  1440
ccugauucau acccaucaga acccaucuuu guuucucacc cagaugccuu ggaagaagau  1500
gaugguguag uucugagugu ggugugagc ccaggagcag acaaaagcc ugcuuaucuc  1560
cugauucuga augccaagga cuuaagugaa guugcccggg cugaaguggga gauuaacauc  1620
ccugucaccu uucauggacu guucaaaaaaa ucuugagcau acuccagcaa gauauguuuu  1680
ugguagcaaa acugagaaaa ucagcuucag gucugcaauc aaauucuguu caauuuuagc  1740
cugcuauaug ucauggutuuu aacuugcaga ugcgcacaau uuugcaaugu uuuacagaaa  1800
gcacugaguu gagcaagcaa uuccuuuauu uaaaaaaaaa aguacguauu uagauaauca  1860
uacuuccucu gugagacagg ccauaacuga aaaacucuua aauauuuagc aaucaaauag  1920
gaaaugaaug uggacuuacu aaauggcuuu uaauuccuau uauaagagca uauuuuaggu  1980
accuaucugc uccaauuaua uuuuuaacau uuaaaaacca aagcccucua cacuugauuu  2040
```

-continued

| | |
|---|---|
| auauuauaug uggcuuugcu gagucaagga aguaucaugc aauaaggcuu aauuacuaaa | 2100 |
| ugucaaacca aacuuuuucu caaaccaggg acuaucaucu aagauuaauu acaguaauua | 2160 |
| uuuugcguau acguaacugc ucaaagauua ugaaucuuau gaauguuaac cuuccguuu | 2220 |
| auuacaagca aguacuauua uuucugauuu uauaauaaga aaaucugugu uuaaucaacu | 2280 |
| gaggccucuc aaccaaauaa caucucagag auuaaguuau auauuaaaag cuuauguaac | 2340 |
| auaaaagcaa guacauauag uagugacuau auuuaaaaaa acagcauaaa augcuuaaaa | 2400 |
| auguaauauu uacuaaaauc agauuauggg auaauguugc aggauuauac uuuauugcau | 2460 |
| cuuuuugguu uaauuguauu uaagcauugu gcaucacuu gggaaaaaua uuaaauuauu | 2520 |
| aacauugagg uauuaauaca uuuuaagccu uuuguuuuua aauucuuuu cuuccagaga | 2580 |
| uuguuuaaaa auaaauauug acaaaaau | 2608 |

<210> SEQ ID NO 23
<211> LENGTH: 1862
<212> TYPE: RNA
<213> ORGANISM: Mouse

<400> SEQUENCE: 23

| | |
|---|---|
| uccucauccu acagcuggua ccagaacucu cucuaaucuu cacuggaaga aaaugucuau | 60 |
| ccaaauugaa cacccugcug guggcuacaa gaaacuauuu gaaacugugg aggaacuguc | 120 |
| cucaccacua acagcucaug ucacaggcag gauuccccuc uggcucacug gcagcucccu | 180 |
| ccgauguggg ccagggcucu uugaaguugg aucugagccu uucuaucacc uguuugaugg | 240 |
| acaagcccuu uugcacaagu uugacuucaa ggagggccau gucacauacc acagaagauu | 300 |
| caucccgcacu gaugcuuaug uucgagcaau gacugagaag aggauuguca uaacagaauu | 360 |
| uggcaccugu gcuuucccag accccugcaa gaauauauuu uccagguuuu uucuuacuu | 420 |
| uaaaggagua gagguuacug acaaugcccu guaaauauc uacccagugg gagaagauua | 480 |
| cuaugcaugc acagagacca acuuuaucac aaagauuaac ccagagaccu uggagacaau | 540 |
| uaagcagguu gaucuuugca acuauauuuc ugcaauggu gccacugcuc auccacauau | 600 |
| ugaaagugau ggaacaguuu acaacauugg gaauugcuuu ggaaaaaauu uuacaguugc | 660 |
| cuacaacauu auuaagaucc cuccacugaa agcagacaag gaagauccaa uaaacaaguc | 720 |
| agaaguugu gugcaguucc ccugcaguga ucguuucaag ccaucuuaug uacacaguuu | 780 |
| uggucugacu cccaacuaua ucguuuuugu ggagacucca gucaaauua accuuuucaa | 840 |
| guuucuuucu ucguggaguc uuggggagc caacuacaug gacuguuucg aguccaauga | 900 |
| aagcauggg guuggcuuc auguugcuga uaaaaaaga agaaaauacu ucaauaacaa | 960 |
| auacaggacu uccccuuuca aucucuucca ucauaucaau acuuaugaag acaauggau | 1020 |
| ucugauugug gaucucuguu gcuggaaagg guuugaauuu guuuauaauu acuuauauuu | 1080 |
| agccaauuua cgugagaauu gggaagaagu uaaaagaaau gcaugaagg cuccucagcc | 1140 |
| ugaagucagg agauauguac uuccuuugac aauugacaag gucgacacag gcagaaauuu | 1200 |
| agucacacug ccccauacaa cugccacagc cacucgcgc agugaugaga ccauauggcu | 1260 |
| ggaaccugag guucucuuuu cagggccucg ucaagccuuu gaauuccuc aaaucaauua | 1320 |
| ccagaaauuu ggagggaaac cuuauacuua ugcaucggaa cuuggguuga ucacuuugu | 1380 |
| uccugacaag cucuguaaga ugaacgucaa aacuaaagaa aucuggaugu ggcaagagcc | 1440 |
| agauucuuac ccaucugaac ccaucuuugu uucaaccca gaugcucugg aagaagauga | 1500 |
| ugguguggu cugagugugg uggugagccc uggggcaggg caaaagccug cauaucuccu | 1560 |

```
gguucugaauu gccaaagacu ugagugaaau ugccagggcu gaaguggaga cuaauauccc    1620
ugugaccuuc cauggacugu ucaaaagauc cugaacauau uccagagaug gcucagcagu    1680
acaacacuga cugcccuucu acagaucgug uguucaauuc ccaaagauca ccuggugacu    1740
cacuuccauc ugagacggaa uccaaugccc ucuuaugcug uuucugaaga cagcaaaagu    1800
guacucauau auacauauga uaaauaaauc uuuaaaaaaa acaaaaaaaa aaaaaaaaaa    1860
aa                                                                   1862

<210> SEQ ID NO 24
<211> LENGTH: 46
<212> TYPE: RNA
<213> ORGANISM: artificial sequence
<220> FEATURE:
<223> OTHER INFORMATION: Mouse RPE65 UUC  376 Hammerhead Ribozyme

<400> SEQUENCE: 24
ucgacggucu ggcugaugag gccgaaaggc cgaaaaagca ccugca                     46

<210> SEQ ID NO 25
<211> LENGTH: 15
<212> TYPE: RNA
<213> ORGANISM: Mouse

<400> SEQUENCE: 25
gugcuuuccc agacc                                                       15

<210> SEQ ID NO 26
<211> LENGTH: 46
<212> TYPE: RNA
<213> ORGANISM: artificial sequence
<220> FEATURE:
<223> OTHER INFORMATION: Mouse RPE65 UUA  480 Hammerhead Ribozyme
      sequence

<400> SEQUENCE: 26
ucgacugcau agcugaugag gccgaaaggc cgaaaaucuu ccugca                     46

<210> SEQ ID NO 27
<211> LENGTH: 15
<212> TYPE: RNA
<213> ORGANISM: Mouse

<400> SEQUENCE: 27
gaagauuacu augca                                                       15

<210> SEQ ID NO 28
<211> LENGTH: 46
<212> TYPE: RNA
<213> ORGANISM: artificial sequence
<220> FEATURE:
<223> OTHER INFORMATION: Mouse RPE65 GUC  1183 Hammerhead Ribozyme
      sequence

<400> SEQUENCE: 28
ucgaccugug uccugaugag gccgaaaggc cgaaaccuug ucugca                     46

<210> SEQ ID NO 29
<211> LENGTH: 15
<212> TYPE: RNA
<213> ORGANISM: Mouse

<400> SEQUENCE: 29
acaaggucga cacag                                                       15
```

```
<210> SEQ ID NO 30
<211> LENGTH: 49
<212> TYPE: RNA
<213> ORGANISM: artificial sequence
<220> FEATURE:
<223> OTHER INFORMATION: Human RPE65 221 shRNA sequence

<400> SEQUENCE: 30
cauuuuacca ccuguuugau ucaagagauc aaacaggugg uaaaauguu        49

<210> SEQ ID NO 31
<211> LENGTH: 49
<212> TYPE: RNA
<213> ORGANISM: artificial sequence
<220> FEATURE:
<223> OTHER INFORMATION: Human RPE65 520 shRNA sequence

<400> SEQUENCE: 31
aauccagaga ccuuggagau ucaagagauc uccaaggucu cuggauuuu        49

<210> SEQ ID NO 32
<211> LENGTH: 49
<212> TYPE: RNA
<213> ORGANISM: artificial sequence
<220> FEATURE:
<223> OTHER INFORMATION: Human RPE65 933 shRNA sequence

<400> SEQUENCE: 32 caaaaaagg aaaaguacu ucaagagagu acuuuuccu uuuuuguu            49

<210> SEQ ID NO 33
<211> LENGTH: 49
<212> TYPE: RNA
<213> ORGANISM: artificial sequence
<220> FEATURE:
<223> OTHER INFORMATION: Human RPE65 2108 shRNA sequence

<400> SEQUENCE: 33
ccaaacuuuu ucucaaaccu ucaagagagg uuugagaaaa aguuugguu        49
```